US011134675B2

United States Patent
Morgenstern et al.

(10) Patent No.: US 11,134,675 B2
(45) Date of Patent: Oct. 5, 2021

(54) METHODS AND COMPOSITIONS FOR DELIVERY OF POLYNUCLEOTIDES

(71) Applicant: MONSANTO TECHNOLOGY LLC, St. Louis, MO (US)

(72) Inventors: David A. Morgenstern, Creve Coeur, MO (US); Lamtho L. Nguyen Ohtake, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 22 days.

(21) Appl. No.: 16/062,008

(22) PCT Filed: Dec. 14, 2016

(86) PCT No.: PCT/US2016/066647
§ 371 (c)(1),
(2) Date: Jun. 13, 2018

(87) PCT Pub. No.: WO2017/106339
PCT Pub. Date: Jun. 22, 2017

(65) Prior Publication Data
US 2018/0360030 A1 Dec. 20, 2018

Related U.S. Application Data

(60) Provisional application No. 62/267,112, filed on Dec. 14, 2015.

(51) Int. Cl.
A01N 25/22 (2006.01)
C12N 15/87 (2006.01)
A61K 47/61 (2017.01)
A01N 43/16 (2006.01)
A01N 25/06 (2006.01)
C12N 15/11 (2006.01)
A01N 63/60 (2020.01)
A01N 25/02 (2006.01)
A01N 25/04 (2006.01)
A01N 25/10 (2006.01)
A01N 57/16 (2006.01)
C12N 15/113 (2010.01)

(52) U.S. Cl.
CPC ............ A01N 25/22 (2013.01); A01N 25/02 (2013.01); A01N 25/04 (2013.01); A01N 25/06 (2013.01); A01N 25/10 (2013.01); A01N 43/16 (2013.01); A01N 57/16 (2013.01); A01N 63/60 (2020.01); A61K 47/61 (2017.08); C12N 15/111 (2013.01); C12N 15/87 (2013.01); C12N 15/113 (2013.01); C12N 2310/14 (2013.01); C12N 2310/351 (2013.01); C12N 2320/32 (2013.01); C12N 2320/51 (2013.01); C12N 2320/52 (2013.01)

(58) Field of Classification Search
CPC ........ A01N 25/22; A01N 33/12; A01N 37/16; A01N 43/16; A01N 63/00; A01N 25/10; A01N 25/06
See application file for complete search history.

(56) References Cited

U.S. PATENT DOCUMENTS

2002/0146826 A1 10/2002 Domb
2004/0098761 A1 5/2004 Trick et al.
2006/0021087 A1 1/2006 Baum et al.

FOREIGN PATENT DOCUMENTS

WO WO 2005/110068 A2 11/2005

OTHER PUBLICATIONS

Baum et al., "Control of coleopteran insect pests through RNA interference" Nature Biotechnol., 25:1322-1326, (2007).
Erdmann et al., "The non-coding RNAs as riboregulators," Nucleic Acids Res., 29(1):189-193 (2001).
Fire et al., "Potent and specific genetic interference by double-stranded RNA in Caenorhabditis elegans," Nature, 391:806-811 (1998).
Gan et al., "Modulation of surface charge, particle size and morphological properties of chitosan-TPP nanoparticles intended for gene delivery," Colloids and Surfaces B: Biointerfaces, 44:65-73 (2005).
Gong et al., "Silencing of Rieske iron-sulfur protein using chemically synthesized siRNA as a potential biopesticide against Plutella xylostella," Pest Manag. Sci., 67:514-520 (2011).
Gottesman, "Micros for microbes: non-coding regulatory RNAs in bacteria," Trends Genet., 21(7):399-404 (2005).
Griffiths-Jones et al., "Rfam: annotating non-coding RNAs in complete genomes," Nucleic Acids Res., 33:121-124 (2005).
Huang et al., "Engineering broad root-knot resistance in transgenic plants by RNAi silencing of a conserved and essential root-knot nematode parasitism gene," Proc. Natl. Acad. Sci. USA, 103:14302-14306 (2006).
International Search Report and Written Opinion dated Feb. 28, 2019, in International Patent Application No. PCT/US16/66647.
Kumar et al., "Bead Form of Guaran Gel for Chromatographic Column Packing," Reactive Polymers, 21:141-3 (1993).
Li et al., "RNA interference in Nilaparvata lugens (Homoptera: Delphacidae) based on dsRNA ingestion," Pest Manag. Sci., 67:852-859 (2011).

(Continued)

Primary Examiner — Hasan S Ahmed
(74) Attorney, Agent, or Firm — Arnold & Porter Kaye Scholer LLP; Amanda Carmany-Rampey; David R. Marsh

(57) ABSTRACT

This disclosure provides compositions and methods for delivery of a polynucleotide to an organism. More specifically, this disclosure relates to compositions including a mixture of a polynucleotide and a cationic polysaccharide, and methods of providing such compositions to an organism, such as a pest (e.g., an insect, a nematode, a mollusk).

16 Claims, No Drawings

(56) References Cited

OTHER PUBLICATIONS

Mao et al., "Silencing a cotton bollworm P450 monooxygenase gene by plant-mediated RANi impairs larval tolerance of gossypol," *Nature Biotechnol.*, 25:1307-1313 (2007).
Pitino et al., "Silencing of Aphid Genes by dsRNA Feeding from Plants," *PLoS ONE*, 6(10-e25709):1-8 (2011).
Pridgeon et al., "Topically Applied AaeIAP1 Double-Stranded RNA Kills Female Adults in *Aedes aegypti*," *J. Med. Entomol.*, 45(3):414-420 (2008).
Sindhu et al., "Effective and specific in planta RNAi in cyst nematodes: expression interference of four parasitism genes reduces parasitic success," *J. Exp. Botany*, 60(1):315-324 (2008).
Thompson et al., "Clustal W: improving the sensitivity of progressive multiple sequence alignment through sequence weighting, position-specific gap penalties and weight matrix choice," *Nucl. Acids Res.*, 22(22):4673-4680 (1994).
Timmons and Fire, "Specific interference by ingested dsRNA," *Nature*, 395:854 (1998).
Upadhyay et al., "RNA interference for the control of whiteflies (*Bemisia tabaci*) by oral route," *J. Biosci.*, 36(1):153-161 (2011).
Whyard et al., "Ingested double-stranded RNAs can act as species-specific insecticides," *Insect Biochem. Mol. Biol.*, 39:824-832 (2009).

METHODS AND COMPOSITIONS FOR DELIVERY OF POLYNUCLEOTIDES

CROSS REFERENCE TO RELATED APPLICATIONS

This application is a U.S. National Stage of International Application No. PCT/US2016/066647, filed Dec. 14, 2016, which claims priority to U.S. Provisional Application No. 62/267,112, filed Dec. 14, 2015, both of which are incorporated by reference in their entirety herein.

FIELD

Disclosed herein are compositions and methods for delivery of a polynucleotide to an organism. More specifically, this disclosure relates to compositions including a mixture of a polynucleotide and a cationic polysaccharide, and methods of providing such compositions to an organism, such as a pest (e.g., an insect, a nematode, a mollusk).

BACKGROUND

Commercial crops are often the targets of attack by invertebrate pests such as insects. RNA interference (RNAi, RNA-mediated gene suppression) is a selective and environmentally-friendly approach to pest control. RNAi-based gene suppression was first demonstrated in nematodes (Fire et al., (1998) *Nature,* 391:806-811; Timmons & Fire (1998) *Nature,* 395:854). Subsequently, RNAi-based suppression of genes using recombinant nucleic acid techniques has been reported in a number of invertebrate species, including agriculturally or economically important pests from various insect and nematode taxa, such as: root-knot nematodes (*Meloidogyne* spp.), see Huang et al. (2006) *Proc. Natl. Acad. Sci. USA,* 103:14302-14306, doi:10.1073/pnas.0604698103); cotton bollworm (*Helicoverpa armigera*), see Mao et al. (2007) *Nature Biotechnol.,* 25:1307-1313, doi:10.1038/nbt1352; Western corn rootworm (*Diabrotica virgifera* LeConte), see Baum et al. (2007) *Nature Biotechnol.,* 25:1322-1326, doi:10.1038/nbt1359; sugar beet cyst nematode (*Heterodera schachtii*), see Sindhu et al. (2008) *J. Exp. Botany,* 60:315-324, doi:10.1093/jxWern289; mosquito (*Aedes aegypti*), see Pridgeon et al. (2008) *J. Med. Entomol.,* 45:414-420, fruit flies (*Drosophila melanogaster*), flour beetles (*Tribolium castaneum*), pea aphids (*Acyrthosiphon pisum*), and tobacco hornworms (*Manduca sexta*), see Whyard et al. (2009) *Insect Biochem. Mol. Biol.,* 39:824-832; diamondback moth (*Plutella xylostella*), see Gong et al. (2011) *Pest Manag. Sci.,* 67: 514-520; green peach aphid (*Myzus persicae*), see Pitino et al. (2011) *PLoS ONE,* 6:e25709; brown planthopper (*Nilaparvata lugens*), see Li et al. (2011) *Pest Manag. Sci.,* 67:852-859; and whitefly (*Bemisia tabaci*), see Upadhyay et al. (2011) *J. Biosci.,* 36:153-161.

In order to unlock the full potential of RNAi for pest control, there is a need for methods and compositions that improve the stability of interfering RNAs in topical applications, where the interfering RNA is exposed to a variety of environmental conditions, such as precipitation and photodegradation.

SUMMARY

Several embodiments are related to a composition including a cross-linked cationic polysaccharide particle and a polynucleotide. Related embodiments include formulations including a composition including a cross-linked cationic polysaccharide and a polynucleotide. The complex formed by the polynucleotide and the cross-linked cationic polysaccharide particle can be included in liquid or solid formulations, for example, dry powders or spray formulations suitable for agricultural use.

Several embodiments are related to a method of increasing the stability of a polynucleotide including the step of combining a cross-linked cationic polysaccharide particle with a polynucleotide to form a particle. Other embodiments are related to a method of improving the rainfastness of a polynucleotide, including the step of combining a polynucleotide with a cross-linked cationic polysaccharide particle to form a cationic, hydrophilic complex. Other embodiments are related to a method of improving the photostability of a polynucleotide, including the step of combining a polynucleotide with a cross-linked cationic polysaccharide particle to form a cationic, hydrophilic complex.

Several embodiments are related to a composition including a cationic guar gum, and a polynucleotide. Related embodiments include formulations including a composition including a cationic guar gum, and a polynucleotide. The complex formed by the polynucleotide and the cationic guar gum can be included in liquid or solid formulations, for example, dry powders or spray formulations suitable for agricultural use. Embodiments of such formulations further include other components, such as, but not limited to, silicas, surfactants, and dispersants.

Several embodiments are related to a method of increasing the stability of a polynucleotide including the step of combining a cationic guar gum with a polynucleotide to form a particle. Other embodiments are related to a method of improving the rainfastness of a polynucleotide, including the step of combining a polynucleotide with a cationic guar gum to form a cationic, hydrophilic complex. Other embodiments are related to a method of improving the photostability of a polynucleotide, including the step of combining a polynucleotide with a cationic guar gum to form a cationic, hydrophilic complex.

Several embodiments relate to a composition comprising: one or more cationic polysaccharides and one ore more polynucleotides. In some embodiments, the polynucleotide and the cationic polysaccharide are bound by electrostatic attraction to form a complex. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic polysaccharide comprises one or more of any combination of a glucan, a galactan, a galactomannan, or any a derivative thereof. In some embodiments, the glucan is selected from the group consisting of starch, amylose, amylopectin, dextran, maltodextrin, cellulose, and a derivative thereof. In some embodiments, the galactan comprises agar or a derivative thereof. In some embodiments, the galactomannan is selected from the group consisting of guar gum, locust bean gum, tara gum, fenugreek gum and a derivative thereof. In some embodiments, the derivative of the glucan and/or the galacan comprises one or more of chitin, chitosan, and carrageenan. In some embodiments, the cationic polysaccharide is a cross-linked cationic polysaccharide. In some embodiments, the cross-linked cationic polysaccharide comprises a monomeric unit selected from the group consisting of glucose, galactose, fructose, mannose, glucosamine, N-acetylglucosamine, galactosamine, guar, a derivative thereof, and combinations thereof. In some embodiments, the one or more cationic polysaccharides and one or more polynucleotides form a complex that having at least one dimension that exceeds 200 nanometers. In some embodiments, the one ore more cationic polysaccharides and one or more polynucleotides form a complex having at least one dimension that exceeds 500 nanometers. In some embodiments, the one ore more cationic polysaccharides and one or more polynucleotides form a porous, hydrophilic particle. In some embodiments the composition is non-soluble in an aqueous solution. In some embodiments the composition is provided as an aqueous suspension. In some embodiments, the cationic polysaccharide is a cross-linked cationic polysaccharide comprising one or more cationic functional groups. In some embodiments, the one or more cationic functional groups comprises an amine or an ammonium cation. In some embodiments, the amine or the ammonium cation is one or more selected from the group consisting of a primary amine, a secondary amine, a tertiary amine, and a quaternary ammonium cation. In some embodiments, the amine or the ammonium cation is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the amine or the ammonium cation is one or more selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments, the R1, R2, R3, and R4 are each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. In some embodiments, the C1-C6 alkyl is selected from the group consisting of methyl, ethyl, propyl, butyl, 3-pentyl and hexyl, each of which may be optionally independently substituted with one or more of hydroxyl (—OH). In some embodiments, one or more cationic functional groups is positively charged at the pH of the aqueous suspension. In some embodiments, the cationic functional group comprises a 2-hydroxypropyl trimethylammonium cation. In some embodiments, the cross-linked cationic polysaccharide has a content of a cationic functional group per monomeric unit of the cross-linked cationic polysaccharide in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the cross-linked cationic polysaccharide is provided by reaction of a non-cross-linked polysaccharide with an alkylating agent. In some embodiments, the alkylating agent is glycidyl trimethylammonium chloride (GTAC). In some embodiments, the non-cross-linked polysaccharide is starch or guar gum. In some embodiments, the non-cross-linked polysaccharide is a starch selected from the group consisting of: corn starch, potato starch, rice starch, tapioca starch, and wheat starch. In some embodiments, the GTAC is present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. In some embodiments, the cross-linked cationic polysaccharide is provided by reaction of a non-cross-linked polysaccharide with diacid chlorides of dicarboxylic acids or with diglycidyl ethers. In some embodiments, the cross-linked cationic polysaccharide is provided by reaction of a non-cross-linked polysaccharide with phosphoryl chloride (POCl3), diglycidyl polyethylene glycol (PEG), diglycidyl bisphenol A, and diglycidyl 1,4-butanediol, oxalyl chloride, phthaloyl chloride, adipoyl chloride. In some embodiments, the cross-linked cationic polysaccharide is provided by reaction of a non-cross-linked starch with glycidyl trimethylammonium chloride (GTAC) and with phosphoryl chloride (POCl3). In some embodiments, the POCl3 is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. In some embodiments, the ratio (w/w) of cross-linked cationic polysaccharide to polynucleotide is 0.2:1 to 50:1. In several embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant. In some embodiments, the cross-linked cationic polysaccharide particles are not soluble in water. In some embodiments, the complex comprising the polynucleotide and the cationic polysaccharide is purified by addition of a displacement agent to a composition comprising the polynucleotide, cationic polysaccharide and a silicate, whereby the polynucleotide/cationic polysaccharide complex is displaced from the silicate, thereby providing a purified polynucleotide/cationic polysaccharide composition. In some embodiments, the displacement agent is a tertiary amine, an ammonium salt, or a water-soluble polar polymer. In some embodiments, the displacement agent is polyvinylpyrrolidone, dimethyl distearyl ammonium chloride.

Several embodiments relate to a method of increasing the stability of a polynucleotide comprising: contacting a cationic polysaccharide with a polynucleotide to form a particle. In some embodiments, the polynucleotide and the cationic polysaccharide are bound by electrostatic attraction to form a particle. In some embodiments, the cationic polysaccharide comprises one or more of any combination of a glucan, a galactan, a galactomannan, or any a derivative thereof. In some embodiments, the glucan is selected from the group consisting of starch, amylose, amylopectin, dextran, maltodextrin, cellulose, and a derivative thereof. In some embodiments, the galactan comprises agar or a derivative thereof. In some embodiments, the galactomannan is selected from the group consisting of guar gum, locust bean gum, tara gum, fenugreek gum and a derivative thereof. In some embodiments, the derivative of the glucan and/or the galacan comprises one or more of chitin, chitosan, and carrageenan. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic polysaccharide is a cross-linked cationic polysaccharide. In some embodiments, the cross-linked cationic polysaccharide comprises a monomeric unit selected from the group consisting of glucose, galactose, fructose, mannose, glucosamine, N-acetylglucosamine, galactosamine, guar, a derivative thereof, and combinations thereof. In some embodiments, the one or more cationic polysaccharides and one or more polynucleotides form a particle that having at least one dimension that exceeds 200 nanometers. In some embodiments, the one ore more cationic polysaccharides and one or more polynucleotides form a particle having at least one dimension that exceeds 500 nanometers. In some embodiments, the one ore more cationic polysaccharides and one or more polynucleotides form a porous, hydrophilic particle. In some embodiments the particle is non-soluble in an aqueous solution. In some embodiments the particle is provided in an aqueous suspension. In some embodiments, the cationic polysaccharide is a cross-linked cationic polysaccharide comprising one or more cationic functional groups. In some embodiments, the one or more cationic functional groups comprises an amine or an ammonium cation. In some embodiments, the amine or the ammonium cation is one or more selected from the group consisting of a primary amine, a secondary amine, a tertiary amine, and a quaternary ammonium cation. In some embodiments, the amine or the ammonium cation is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the amine or the ammonium cation is one or more selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments, the R1, R2, R3, and R4 are each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. In some embodiments, the C1-C6 alkyl is selected from the group consisting of methyl, ethyl, propyl, butyl, 3-pentyl and hexyl, each of which may be optionally independently substituted with one or more of hydroxyl (—OH). In some embodiments, one or more cationic functional groups is positively charged at the pH of the aqueous suspension. In some embodiments, the cationic functional group comprises a 2-hydroxypropyl trimethylammonium cation. In some embodiments, the cross-linked cationic polysaccharide has a content of a cationic functional group per monomeric unit of the cross-linked cationic polysaccharide in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the cross-linked cationic polysaccharide is provided by reaction of a non-cross-linked polysaccharide with an alkylating agent. In some embodiments, the alkylating agent is glycidyl trimethylammonium chloride (GTAC). In some embodiments, the non-cross-linked polysaccharide is starch or guar gum. In some embodiments, the non-cross-linked polysaccharide is a starch selected from the group consisting of: corn starch, potato starch, rice starch, tapioca starch, and wheat starch. In some embodiments, the GTAC is present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. In some embodiments, the cross-linked cationic polysaccharide is provided by reaction of a non-cross-linked polysaccharide with diacid chlorides of dicarboxylic acids or with diglycidyl ethers. In some embodiments, the cross-linked cationic polysaccharide is provided by reaction of a non-cross-linked polysaccharide with phosphoryl chloride (POCl3), diglycidyl polyethylene glycol (PEG), diglycidyl bisphenol A, and diglycidyl 1,4-butanediol, oxalyl chloride, phthaloyl chloride, adipoyl chloride. In some embodiments, the cross-linked cationic polysaccharide is provided by reaction of a non-cross-linked starch with glycidyl trimethylammonium chloride (GTAC) and with phosphoryl chloride (POCl3). In some embodiments, the POCl3 is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. In some embodiments, the ratio (w/w) of cross-linked cationic polysaccharide to polynucleotide is 0.2:1 to 50:1. In several embodiments, the particle is provided in a composition further comprising one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant. In some embodiments, the cross-linked cationic polysaccharide particles are not soluble in water. In some embodiments, the complex comprising the polynucleotide and the cross-linked cationic polysaccharide is purified by addition of a displacement agent to a composition comprising the polynucleotide, cross-linked cationic polysaccharide and a silicate, whereby the polynucleotide/cross-linked cationic polysaccharide complex is displaced from the silicate, thereby providing a purified polynucleotide/cross-linked cationic polysaccharide composition. In some embodiments, the displacement agent is a tertiary amine, an ammonium salt, or a water-soluble polar polymer. In some embodiments, the displacement agent is polyvinylpyrrolidone, dimethyl distearyl ammonium chloride Several embodiments relate to a method of improving the rainfastness of a polynucleotide, comprising: combining a polynucleotide with a cross-linked cationic polysaccharide particle to form a cationic, hydrophilic complex. In some embodiments, the complex further comprises a photoprotectant. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic polysaccharide comprises one or more of any combination of a glucan, a galactan, a galactomannan, or any a derivative thereof. In some embodiments, the glucan is selected from the group consisting of starch, amylose, amylopectin, dextran, maltodextrin, cellulose, and a derivative thereof. In some embodiments, the galactan comprises agar or a derivative thereof. In some embodiments, the galactomannan is selected from the group consisting of guar gum, locust bean gum, tara gum, fenugreek gum and a derivative thereof. In some embodiments, the derivative of the glucan and/or the galacan comprises one or more of chitin, chitosan, and carrageenan. In some embodiments, the cationic polysaccharide is a cross-linked cationic polysaccharide. In some embodiments, the cross-linked cationic polysaccharide comprises a monomeric unit selected from the group consisting of glucose, galactose, fructose, mannose, glucosamine, N-acetylglucosamine, galactosamine, guar, a derivative thereof, and combinations thereof. In some embodiments, the one or more cationic polysaccharides and one or more polynucleotides form a complex that having at least one dimension that exceeds 200 nanometers. In some embodiments, the one ore more cationic polysaccharides and one or more polynucleotides form a complex having at least one dimension that exceeds 500 nanometers. In some embodiments, the one ore more cationic polysaccharides and one or more polynucleotides form a porous, hydrophilic particle. In some embodiments the composition is non-soluble in an aqueous solution. In some embodiments the composition is provided as an aqueous suspension. In some embodiments, the cationic polysaccharide is a cross-linked cationic polysaccharide comprising one or more cationic functional groups. In some embodiments, the one or more cationic functional groups comprises an amine or an ammonium cation. In some embodiments, the amine or the ammonium cation is one or more selected from the group consisting of a primary amine, a secondary amine, a tertiary amine, and a quaternary ammonium cation. In some embodiments, the amine or the ammonium cation is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the amine or the ammonium cation is one or more selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments, the R1, R2, R3, and R4 are each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. In some embodiments, the C1-C6 alkyl is selected from the group consisting of methyl, ethyl, propyl, butyl, 3-pentyl and hexyl, each of which may be optionally independently substituted with one or more of hydroxyl (—OH). In some embodiments, one or more cationic functional groups is positively charged at the pH of the aqueous suspension. In some embodiments, the cationic functional group comprises a 2-hydroxypropyl trimethylammonium cation. In some embodiments, the cross-linked cationic polysaccharide has a content of a cationic functional group per monomeric unit of the cross-linked cationic polysaccharide in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the cross-linked cationic polysaccharide is provided by reaction of a non-cross-linked polysaccharide with an alkylating agent. In some embodiments, the alkylating agent is glycidyl trimethylammonium chloride (GTAC). In some embodiments, the non-cross-linked polysaccharide is starch or guar gum. In some embodiments, the non-cross-linked polysaccharide is a starch selected from the group consisting of: corn starch, potato starch, rice starch, tapioca starch, and wheat starch. In some embodiments, the GTAC is present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. In some embodiments, the cross-linked cationic polysaccharide is provided by reaction of a non-cross-linked polysaccharide with diacid chlorides of dicarboxylic acids or with diglycidyl ethers. In some embodiments, the cross-linked cationic polysaccharide is provided by reaction of a non-cross-linked polysaccharide with phosphoryl chloride (POCl3), diglycidyl polyethylene glycol (PEG), diglycidyl bisphenol A, and diglycidyl 1,4-butanediol, oxalyl chloride, phthaloyl chloride, adipoyl chloride. In some embodiments, the cross-linked cationic polysaccharide is provided by reaction of a non-cross-linked starch with glycidyl trimethylammonium chloride (GTAC) and with phosphoryl chloride (POCl3). In some embodiments, the POCl3 is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. In some embodiments, the ratio (w/w) of cross-linked cationic polysaccharide to polynucleotide is 0.2:1 to 50:1. In several embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant. In some embodiments, the cross-linked cationic polysaccharide particles are not soluble in water.

Several embodiments relate to a composition comprising: a cationic guar gum, and one or more polynucleotides. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. Several embodiments relate to composition comprising a dsRNA molecule and a linear cationic guar gum. Several embodiments relate to composition comprising dsRNA and a cross-linked cationic guar gum. In some embodiments, the cross-linked cationic guar gum comprises a cationic functional group per monomeric unit of the cross-linked cationic guar in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the one or more cationic functional groups comprises an amine. In some embodiments, the amine is one or more selected from the group consisting of a primary amine, a secondary amine, a tertiary amine, and a quaternary ammonium cation. In some embodiments, the cationic guar gum is a cross-linked by reaction of a linear cationic guar gum with one or more cross-linking agents. In some embodiments, one or more cross-linking agents are selected from the group consisting of diacid chlorides of dicarboxylic acids, diglycidyl ethers, phosphoryl chloride (POCl3), diglycidyl polyethylene glycol (PEG), diglycidyl bisphenol A, diglycidyl 1,4-butanediol, oxalyl chloride, phthaloyl chloride, and adipoyl chloride. In some embodiments, the amine comprises one or more alkyl, alkene, alkyne, alcohol, aryl, or heteroaryl substituents. In some embodiments, the cationic guar gum is selected from the group consisting of: guar gum, hydroxypropyltrimonium chloride; guar gum, 2-hydroxypropyl 2-hydroxy-3-(trimethylammonio)propyl ether, chloride; hydroxypropyl cationic guar (mol. wt. of 2 million Dalton); and cationic guar (mol. wt. of 2 million Dalton). In some embodiments, the one or more polynucleotides and the cationic guar gum are bound by electrostatic attraction to form a complex. In some embodiments, the complex has at least one dimension that exceeds 200 nanometers. In some embodiments, the complex has at least one dimension that exceeds 500 nanometers. In some embodiments, the complex has at least one dimension that exceeds 1 micrometer. In some embodiments, the cationic guar gum and one or more polynucleotides comprise a porous, hydrophilic particle. In some embodiments, the cationic guar gum and one or more polynucleotides form a complex that is non-soluble in an aqueous solution. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic guar gum comprises one or more of a linear cationic guar gum, a cross-linked cationic guar gum, and a mixture of linear and cross-linked cationic guar gums. In some embodiments, the composition is provided as an aqueous suspension, wettable powder or as a water-dispersible granule. In some embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, and a photo-protectant.

Several embodiments relate to a method of increasing the stability of one or more polynucleotides comprising: combining a cationic guar gum with one or more polynucleotides to form a complex. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. Several embodiments relate to composition comprising a dsRNA molecule and a linear cationic guar gum. Several embodiments relate to composition comprising dsRNA and a cross-linked cationic guar gum. In some embodiments, the cross-linked cationic guar gum comprises a cationic functional group per monomeric unit of the cross-linked cationic guar in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the one or more cationic functional groups comprises an amine. In some embodiments, the amine is one or more selected from the group consisting of a primary amine, a secondary amine, a tertiary amine, and a quaternary ammonium cation. In some embodiments, the cationic guar gum is a cross-linked by reaction of a linear cationic guar gum with one or more cross-linking agents. In some embodiments, one or more cross-linking agents are selected from the group consisting of diacid chlorides of dicarboxylic acids, diglycidyl ethers, phosphoryl chloride (POCl3), diglycidyl polyethylene glycol (PEG), diglycidyl bisphenol A, diglycidyl 1,4-butanediol, oxalyl chloride, phthaloyl chloride, and adipoyl chloride. In some embodiments, the amine comprises one or more alkyl, alkene, alkyne, alcohol, aryl, or heteroaryl substituents. In some embodiments, the cationic guar gum is selected from the group consisting of: guar gum, hydroxypropyltrimonium chloride; guar gum, 2-hydroxypropyl 2-hydroxy-3-(trimethylammonio)propyl ether, chloride; hydroxypropyl cationic guar (mol. wt. of 2 million Dalton); and cationic guar (mol. wt. of 2 million Dalton). In some embodiments, the one or more polynucleotides and the cationic guar gum are bound by electrostatic attraction to form a complex. In some embodiments, the complex has at least one dimension that exceeds 200 nanometers. In some embodiments, the complex has at least one dimension that exceeds 500 nanometers. In some embodiments, the complex has at least one dimension that exceeds 1 micrometer. In some embodiments, the cationic guar gum and one or more polynucleotides comprise a porous, hydrophilic particle. In some embodiments, the cationic guar gum and one or more polynucleotides form a complex that is non-soluble in an aqueous solution. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic guar gum comprises one or more of a linear cationic guar gum, a cross-linked cationic guar gum, and a mixture of linear and cross-linked cationic guar gums. In some embodiments, the composition is provided as an aqueous suspension, wettable powder or as a water-dispersible granule. In some embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, and a photo-protectant.

Several embodiments relate to a method of improving the rainfastness or photostability of a polynucleotide, comprising combining one or more polynucleotides with a cationic guar gum to form a cationic, hydrophilic complex. In some embodiments, the cationic, hydrophilic complex further comprises a photoprotectant. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. Several embodiments relate to composition comprising a dsRNA molecule and a linear cationic guar gum. Several embodiments relate to composition comprising dsRNA and a cross-linked cationic guar gum. In some embodiments, the cross-linked cationic guar gum comprises a cationic functional group per monomeric unit of the cross-linked cationic guar in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the one or more cationic functional groups comprises an amine. In some embodiments, the amine is one or more selected from the group consisting of a primary amine, a secondary amine, a tertiary amine, and a quaternary ammonium cation. In some embodiments, the cationic guar gum is a crosslinked by reaction of a linear cationic guar gum with one or more cross-linking agents. In some embodiments, one or more cross-linking agents are selected from the group consisting of diacid chlorides of dicarboxylic acids, diglycidyl ethers, phosphoryl chloride (POCl3), diglycidyl polyethylene glycol (PEG), diglycidyl bisphenol A, diglycidyl 1,4-butanediol, oxalyl chloride, phthaloyl chloride, and adipoyl chloride. In some embodiments, the amine comprises one or more alkyl, alkene, alkyne, alcohol, aryl, or heteroaryl substituents. In some embodiments, the cationic guar gum is selected from the group consisting of: guar gum, hydroxypropyltrimonium chloride; guar gum, 2-hydroxypropyl 2-hydroxy-3-(trimethylammonio)propyl ether, chloride; hydroxypropyl cationic guar (mol. wt. of 2 million Dalton); and cationic guar (mol. wt. of 2 million Dalton). In some embodiments, the one or more polynucleotides and the cationic guar gum are bound by electrostatic attraction to form a complex. In some embodiments, the complex has at least one dimension that exceeds 200 nanometers. In some embodiments, the complex has at least one dimension that exceeds 500 nanometers. In some embodiments, the complex has at least one dimension that exceeds 1 micrometer. In some embodiments, the cationic guar gum and one or more polynucleotides comprise a porous, hydrophilic particle. In some embodiments, the cationic guar gum and one or more polynucleotides form a complex that is non-soluble in an aqueous solution. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic guar gum comprises one or more of a linear cationic guar gum, a cross-linked cationic guar gum, and a mixture of linear and cross-linked cationic guar gums. In some embodiments, the composition is provided as an aqueous suspension, wettable powder or as a water-dispersible granule. In some embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, and a photo-protectant.

Several embodiments relate to a method of preparing a purified polynucleotide/cationic guar gum composition comprising addition of a displacement agent to a composition comprising a polynucleotide/cationic guar gum complex and a silicate, whereby the polynucleotide/cationic guar gum complex is displaced from the silicate, thereby providing a purified polynucleotide/cationic guar gum composition. In some embodiments, the displacement agent is a tertiary amine, an ammonium salt, or a water-soluble polar polymer. In some embodiments, the displacement agent is polyvinylpyrrolidone, dimethyl distearyl ammonium chloride.

Several embodiments relate to an insecticidal composition comprising: one or more cationic polysaccharides and one ore more polynucleotides. In some embodiments, the polynucleotide and the cationic polysaccharide are bound by electrostatic attraction to form a complex. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic polysaccharide comprises one or more of any combination of a glucan, a galactan, a galactomannan, or any a derivative thereof. In some embodiments, the glucan is selected from the group consisting of starch, amylose, amylopectin, dextran, maltodextrin, cellulose, and a derivative thereof. In some embodiments, the galactan comprises agar or a derivative thereof. In some embodiments, the galactomannan is selected from the group consisting of guar gum, locust bean gum, tara gum, fenugreek gum and a derivative thereof. In some embodiments, the derivative of the glucan and/or the galacan comprises one or more of chitin, chitosan, and carrageenan. In some embodiments, the cationic polysaccharide is a cross-linked cationic polysaccharide. In some embodiments, the cross-linked cationic polysaccharide comprises a monomeric unit selected from the group consisting of glucose, galactose, fructose, mannose, glucosamine, N-acetylglucosamine, galactosamine, guar, a derivative thereof, and combinations thereof. In some embodiments, the one or more cationic polysaccharides and one or more polynucleotides form a complex that having at least one dimension that exceeds 200 nanometers. In some embodiments, the one ore more cationic polysaccharides and one or more polynucleotides form a complex having at least one dimension that exceeds 500 nanometers. In some embodiments, the one ore more cationic polysaccharides and one or more polynucleotides form a porous, hydrophilic particle. In some embodiments the composition is non-soluble in an aqueous solution. In some embodiments the composition is provided as an aqueous suspension. In some embodiments, the cationic polysaccharide is a cross-linked cationic polysaccharide comprising one or more cationic functional groups. In some embodiments, the one or more cationic functional groups comprises an amine or an ammonium cation. In some embodiments, the amine or the ammonium cation is one or more selected from the group consisting of a primary amine, a secondary amine, a tertiary amine, and a quaternary ammonium cation. In some embodiments, the amine or the ammonium cation is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the amine or the ammonium cation is one or more selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments, the R1, R2, R3, and R4 are each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. In some embodiments, the C1-C6 alkyl is selected from the group consisting of methyl, ethyl, propyl, butyl, 3-pentyl and hexyl, each of which may be optionally independently substituted with one or more of hydroxyl (—OH). In some embodiments, one or more cationic functional groups is positively charged at the pH of the aqueous suspension. In some embodiments, the cationic functional group comprises a 2-hydroxypropyl trimethylammonium cation. In some embodiments, the cross-linked cationic polysaccharide has a content of a cationic functional group per monomeric unit of the cross-linked cationic polysaccharide in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the cross-linked cationic polysaccharide is provided by reaction of a non-cross-linked polysaccharide with an alkylating agent. In some embodiments, the alkylating agent is glycidyl trimethylammonium chloride (GTAC). In some embodiments, the non-cross-linked polysaccharide is starch or guar gum. In some embodiments, the non-cross-linked polysaccharide is a starch selected from the group consisting of: corn starch, potato starch, rice starch, tapioca starch, and wheat starch. In some embodiments, the GTAC is present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. In some embodiments, the cross-linked cationic polysaccharide is provided by reaction of a non-cross-linked polysaccharide with diacid chlorides of dicarboxylic acids or with diglycidyl ethers. In some embodiments, the cross-linked cationic polysaccharide is provided by reaction of a non-cross-linked polysaccharide with phosphoryl chloride (POCl3), diglycidyl polyethylene glycol (PEG), diglycidyl bisphenol A, and diglycidyl 1,4-butanediol, oxalyl chloride, phthaloyl chloride, adipoyl chloride. In some embodiments, the cross-linked cationic polysaccharide is provided by reaction of a non-cross-linked starch with glycidyl trimethylammonium chloride (GTAC) and with phosphoryl chloride (POCl3). In some embodiments, the POCl3 is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. In some embodiments, the ratio (w/w) of cross-linked cationic polysaccharide to polynucleotide is 0.2:1 to 50:1. In several embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant.

In some embodiments, the insecticidal composition is in a form selected from the group consisting of a solid, liquid, powder, suspension, emulsion, spray, encapsulation, microbeads, carrier particulates, film, matrix, soil drench, insect diet or insect bait, and seed treatment. In some embodiments, the insecticidal composition is provided in a form that is ingested by the insect, such as in a liquid, emulsion, or powder applied to a plant on which the insect feeds, or in the form of bait. The insecticidal compositions can further include one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. The insecticidal compositions can further include at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In some embodiments, the combination of the recombinant RNA molecule and the pesticidal agent provides a level of insect control that is synergistic, i. e., greater than the sum of the effects of the recombinant RNA molecule and the pesticidal agent components if tested separately.

A method of controlling a pest infestation, comprising providing an insecticidally effective amount of a composition comprising one or more cationic polysaccharides and one ore more polynucleotides in the diet of the pest, wherein the polynucleotide comprises at least 21 contiguous nucleotides that are complementary or identical to a target gene in the pest. In some embodiments, the polynucleotide and the cationic polysaccharide are bound by electrostatic attraction to form a complex. In some embodiments, the composition further comprises a silicate. In some embodiments, the silicate is selected from the group consisting of silicon dioxide, aluminum silicate, magnesium silicate, montmorillonite, kaolinite, bentonite clay, and kaolin clay. In some embodiments, the cationic polysaccharide comprises one or more of any combination of a glucan, a galactan, a galactomannan, or any a derivative thereof. In some embodiments, the glucan is selected from the group consisting of starch, amylose, amylopectin, dextran, maltodextrin, cellulose, and a derivative thereof. In some embodiments, the galactan comprises agar or a derivative thereof. In some embodiments, the galactomannan is selected from the group consisting of guar gum, locust bean gum, tara gum, fenugreek gum and a derivative thereof. In some embodiments, the derivative of the glucan and/or the galacan comprises one or more of chitin, chitosan, and carrageenan. In some embodiments, the cationic polysaccharide is a cross-linked cationic polysaccharide. In some embodiments, the cross-linked cationic polysaccharide comprises a monomeric unit selected from the group consisting of glucose, galactose, fructose, mannose, glucosamine, N-acetylglucosamine, galactosamine, guar, a derivative thereof, and combinations thereof. In some embodiments, the one or more cationic polysaccharides and one or more polynucleotides form a complex that having at least one dimension that exceeds 200 nanometers. In some embodiments, the one ore more cationic polysaccharides and one or more polynucleotides form a complex having at least one dimension that exceeds 500 nanometers. In some embodiments, the one ore more cationic polysaccharides and one or more polynucleotides form a porous, hydrophilic particle. In some embodiments the composition is non-soluble in an aqueous solution. In some embodiments the composition is provided as an aqueous suspension. In some embodiments, the cationic polysaccharide is a cross-linked cationic polysaccharide comprising one or more cationic functional groups. In some embodiments, the one or more cationic functional groups comprises an amine or an ammonium cation. In some embodiments, the amine or the ammonium cation is one or more selected from the group consisting of a primary amine, a secondary amine, a tertiary amine, and a quaternary ammonium cation. In some embodiments, the amine or the ammonium cation is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the amine or the ammonium cation is one or more selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments, the R1, R2, R3, and R4 are each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. In some embodiments, the C1-C6 alkyl is selected from the group consisting of methyl, ethyl, propyl, butyl, 3-pentyl and hexyl, each of which may be optionally independently substituted with one or more of hydroxyl (—OH). In some embodiments, one or more cationic functional groups is positively charged at the pH of the aqueous suspension. In some embodiments, the cationic functional group comprises a 2-hydroxypropyl trimethylammonium cation. In some embodiments, the cross-linked cationic polysaccharide has a content of a cationic functional group per monomeric unit of the cross-linked cationic polysaccharide in an amount of from about 5% to about 50%, from about 5% to about 40%, from about 5% to about 30%, from about 5% to about 20%, from about 10% to about 50%, from about 10% to about 40%, from about 10% to about 30%, or from about 10% to about 20%. In some embodiments, the cross-linked cationic polysaccharide is provided by reaction of a non-cross-linked polysaccharide with an alkylating agent. In some embodiments, the alkylating agent is glycidyl trimethylammonium chloride (GTAC). In some embodiments, the non-cross-linked polysaccharide is starch or guar gum. In some embodiments, the non-cross-linked polysaccharide is a starch selected from the group consisting of: corn starch, potato starch, rice starch, tapioca starch, and wheat starch. In some embodiments, the GTAC is present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. In some embodiments, the cross-linked cationic polysaccharide is provided by reaction of a non-cross-linked polysaccharide with diacid chlorides of dicarboxylic acids or with diglycidyl ethers. In some embodiments, the cross-linked cationic polysaccharide is provided by reaction of a non-cross-linked polysaccharide with phosphoryl chloride (POCl3), diglycidyl polyethylene glycol (PEG), diglycidyl bisphenol A, and diglycidyl 1,4-butanediol, oxalyl chloride, phthaloyl chloride, adipoyl chloride. In some embodiments, the cross-linked cationic polysaccharide is provided by reaction of a non-cross-linked starch with glycidyl trimethylammonium chloride (GTAC) and with phosphoryl chloride (POCl3). In some embodiments, the POCl3 is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In some embodiments, the polynucleotide comprises RNA. In some embodiments, the polynucleotide comprises dsRNA comprising at least 18, at least 19, at least 20, at least 21, at least 22, at least 23, at least 24, at least 25, at least 26, at least 27, at least 28, at least 29, at least 30 or more contiguous nucleotides that are complementary or identical to an essential gene of a target pest. In some embodiments, the ratio (w/w) of cross-linked cationic polysaccharide to polynucleotide is 0.2:1 to 50:1. In several embodiments, the composition further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant. In some embodiments, the cross-linked cationic polysaccharide particles are not soluble in water. In some embodiments, the complex comprising the polynucleotide and the cationic polysaccharide is purified by addition of a displacement agent to a composition comprising the polynucleotide, cationic polysaccharide and a silicate, whereby the polynucleotide/cationic polysaccharide complex is displaced from the silicate, thereby providing a purified polynucleotide/cationic polysaccharide composition. In some embodiments, the displacement agent is a tertiary amine, an ammonium salt, or a water-soluble polar polymer. In some embodiments, the displacement agent is polyvinylpyrrolidone, dimethyl distearyl ammonium chloride.

DETAILED DESCRIPTION

Unless defined otherwise, all technical and scientific terms used herein have the same meaning as commonly understood by one of ordinary skill in the art to which this disclosure belongs. Where a term is provided in the singular, the inventors also contemplate aspects of the invention described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

Any references cited herein are incorporated by reference in their entireties.

As used herein, the singular form "a," "an," and "the" include plural references unless the context clearly dictates otherwise. For example, the term "a compound" or "at least one compound" may include a plurality of compounds, including mixtures thereof.

As used herein, the term "about" indicates that a value includes the inherent variation of error for the method being employed to determine a value, or the variation that exists among experiments.

As used herein, the term "rainfastness" refers to the ability of a substance to withstand being washed off by precipitation, condensation, guttation or irrigation. In one aspect, the substance is a polynucleotide. Any standard methods known in the art, including but not limited to those disclosed in the Examples, can be used to measure rainfastness. In some embodiments, rainfastness is measured by the percentage of a substance, such as but not limited to dsRNA, originally applied onto a location that is still left on the location after one or more episodes of precipitation, condensation, guttation or irrigation. In some embodiments, the amount of a substance originally applied onto a leaf surface can be determined with a control leaf sample that is not exposed to precipitation, condensation, guttation or irrigation.

As used herein, the terms "increasing rainfastness," "increased rainfastness," and "improved rainfastness" refer to at least about 1%, at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase in the percentage of a substance, such as a polynucleotide, remaining on the application site after one or more episodes of precipitation, condensation, guttation or overhead irrigation, when compared with a control that is not complexed with a cationic polysaccharide as described herein.

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Polynucleotides can include ribonucleotides, deoxyribonucleotides or a mixture of ribonucleotides and deoxyribonucleotides. In some embodiments, polynucleotides include non-canonical nucleotides or chemically modified nucleotides as commonly practiced in the art; see, e. g., chemical modifications disclosed in the technical manual "RNA Interference (RNAi) and DsiRNAs", 2011 (Integrated DNA Technologies Coralville, Iowa). Aspects of this disclosure include compositions including oligonucleotides having a length of 16-25 nucleotides (e. g., 16-mers, 17-mers, 18-mers, 19-mers, 20-mers, 21-mers, 22-mers, 23-mers, 24-mers, or 25-mers), or medium-length polynucleotides having a length of 26 or more nucleotides (e. g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length at least about 300 nucleotides (e. g., polynucleotides of from about 300 to about 400 nucleotides, from about 400 to about 500 nucleotides, from about 500 to about 600 nucleotides, from about 600 to about 700 nucleotides, from about 700 to about 800 nucleotides, from about 800 to about 900 nucleotides, from about 900 to about 1000 nucleotides, from about 300 to about 500 nucleotides, from about 300 to about 600 nucleotides, from about 300 to about 700 nucleotides, from about 300 to about 800 nucleotides, from about 300 to about 900 nucleotides, or about 1000 nucleotides in length, or even greater than about 1000 nucleotides in length, for example, up to 2000 nucleotides, 3000 nucleotides, 4000 nucleotides, 5000 nucleotides in length, or up to the entire length of a target gene including coding or non-coding or both coding and non-coding portions of the target gene). The polynucleotides described herein can be single-stranded (ss) or double-stranded (ds) or may include both single-stranded and double-stranded segments. "Double-stranded" refers to the base-pairing that occurs between sufficiently complementary, anti-parallel nucleic acid strands to form a double-stranded nucleic acid structure, generally under physiologically relevant conditions. Embodiments include those wherein the polynucleotide is selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used. Where a polynucleotide is double-stranded, such as the dsRNA described in the Examples, its length can be described in terms of base pairs. Double-stranded polynucleotides, such as the dsRNA described in the working examples, can further be described in terms of one or more of the single-stranded components.

In several embodiments as described herein, polynucleotides, whether DNA or RNA or both, and whether single- or double-stranded, include at least one segment of 21 or more contiguous nucleotides (or, in the case of double-stranded polynucleotides, at least 21 contiguous base-pairs) that are essentially identical or essentially complementary to a fragment of equivalent size of the DNA of a target gene or the target gene's RNA transcript. Throughout this disclosure, "at least 21 contiguous" means "from about 21 to about 10,000, including every whole number point in between". In some embodiments, the polynucleotide comprises at least one segment of 22, 23, 24, 25, 26, 27, 28, 29, 30, 31, 32, 33, 34, 35, 36, 37, 38, 39, 40, 41, 42, 43, 45, 46, 47, 48, 49, 50 or more contiguous nucleotides (or, in the case of double-stranded polynucleotides, at least 22, 23, 24, 25, 26, 27, 28, 29, 30, 31, 32, 33, 34, 35, 36, 37, 38, 39, 40, 41, 42, 43, 45, 46, 47, 48, 49, 50 contiguous base-pairs) that are essentially identical or essentially complementary to a fragment of equivalent size of the DNA of a target gene or the target gene's RNA transcript. In some embodiments, the target gene is an essential gene of a pest.

As used herein, the term "pest" refers to insects, arachnids, crustaceans, fungi, bacteria, viruses, nematodes, flatworms, roundworms, pinworms, hookworms, tapeworms, trypanosomes, mosquitoes, schistosomes, botflies, fleas, ticks, mites, and lice and the like that are pervasive in the human environment and that may ingest or contact one or more cells, tissues, or fluids produced by a pest host or symbiont coated with a composition as described herein or that may ingest plant material coated the polynucleotide composition. Examples of pests include, but are not limited to Coleoptera, Cerambycidae, Chrysomelidae, Coccinellidae, Curculionidae, Elateridae, Meloidae, Scarabaeidae, Tenebrionidae, *Thrips*, Aphids, Corn Earworm, Corn Leafhopper, Corn Leafminer, Cucumber beetles, Cutworms, Flea Beetles, Cutworms, Grasshoppers, Spider mites, Weevels, Wireworms, Colorado potato beetle (*Leptinotarsa decemlineata*), potato leafhopper (*Empoasca fabae*), potato aphid (*Macrosiphum euphorbiae*), green peach aphid (*Myzus persicae*), *Altica ambiens* (alder flea beetle), *Altica canadensis* (prairie flea beetle), *Altica chalybaea* (grape flea beetle), *Altica prasina* (poplar flea beetle), *Altica rosae* (rose flea beetle), *Altica Sylvia* (blueberry flea beetle), *Altica ulmi* (elm flea beetle), *Chaetocnema pulicaria* (corn flea beetle), *Chaetocnema conofinis* (sweet potato flea beetle), *Epitrix cucumeris* (potato flea beetle), *Systena blanda* (palestripped fleabeetle), and *Systena frontalis* (redheaded flea beetle), *Phyllotreta armoraciae* (horseradish flea beetle), *Phyllotreta cruciferae* (canola flea beetle), *Phyllotreta pusilla* (western black flea beetle), *Phyllotreta nemorum* (striped turnip flea beetle), *Phyllotreta atra* (turnip flea beetle), *Phyllotreta robusta* (garden flea beetle), *Phyllotreta striolata* (striped flea beetle), *Phyllotreta undulata, Psylliodes chrysocephala*, and *Psylliodes punctulata* (hop flea beetle).

As used herein, the terms "target gene", "target nucleotide", or "target sequence" refers to a nucleotide sequence that occurs in a gene or gene product against which a polynucleotide that induces and RNAi response is directed. In this context, the term "gene" means a locatable region of genomic sequence, corresponding to a unit of inheritance, which can include regulatory regions, such as promoters, enhancers, 5' untranslated regions, intron regions, 3' untranslated regions, transcribed regions, and other functional sequence regions that may exist as native genes or transgenes in a plant genome. Depending upon the circumstances, the term target sequence or target gene can refer to the full-length nucleotide sequence of the gene or gene product targeted for suppression or the nucleotide sequence of a portion of the gene or gene product targeted for suppression. In some embodiments, the target nucleotide is a messenger RNA. In some embodiments, the target nucleotide is a non-coding RNA. In some embodiments, the target gene is an essential gene of a pest.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may include additions or deletions (gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is the to be identical to the reference sequence and vice-versa. An alignment of two or more sequences may be performed using any suitable computer program. For example, a widely used and accepted computer program for performing sequence alignments is CLUSTALW v1.6 (Thompson, et al., Nucl. Acids Res., 22: 4673-4680, 1994).

By "essentially identical" or "essentially complementary" to a target gene or a fragment of a target gene is meant that a polynucleotide strand (or at least one strand of a double-stranded polynucleotide, such as of a dsRNA capable of inducing RNAi) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. For example, in some embodiments, a polynucleotide has 100 percent sequence identity or at least about 80, 81, 82, 83, 84, 85, 86, 87, 88, 89, 90, 91, 92, 93, 94, 95, 96, 97, 98, or 99 percent sequence identity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a polynucleotide has 100 percent sequence complementarity or at least about 80, 81, 82, 83, 84, 85, 86, 87, 88, 89, 90, 91, 92, 93, 94, 95, 96, 97, 98, or 99 percent sequence complementarity when compared to a sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more contiguous nucleotides in the target gene or RNA transcribed from the target gene. In some embodiments, a polynucleotide has 100 percent sequence identity with or complementarity to one allele or one family member of a given target gene (coding or non-coding sequence of a gene). In some embodiments, a polynucleotide has at least about 80, 81, 82, 83, 84, 85, 86, 87, 88, 89, 90, 91, 92, 93, 94, 95, 96, 97, 98, or 99 percent sequence identity with or complementarity to multiple alleles or family members of a given target gene. In some embodiments, a polynucleotide has 100 percent sequence identity with or complementarity to multiple alleles or family members of a given target gene.

As used herein, the term "cationic polysaccharide" refers to a polysaccharide which bears a net positive charge and has been functionalized with one or more cationic substituent groups by covalent linkage while maintaining the integrity of the polysaccharide chain.

By "insecticidally effective" is meant effective in inducing a physiological or behavioral change in an insect (e. g., adult or larval insects) that infests a plant such as, but not limited to, growth stunting, increased mortality, decrease in reproductive capacity or decreased fecundity, decrease in or cessation of feeding behavior or movement, or decrease in or cessation of metamorphosis stage development.

The term "alkyl" as employed herein, by itself or as part of another group, refers to both straight and branched chain radicals of up to ten carbons. Non-limiting examples of $C_1$-$C_{10}$ alkyl groups include methyl, ethyl, propyl, isopropyl, butyl, sec-butyl, tert-butyl, 3-pentyl, hexyl and octyl groups. For example, the term "alkyl" as used herein, by itself or as part of another group, can refer to a straight or branched chain radical comprising from one to six carbon atoms.

The term "alkenyl" as employed herein, by itself or as part of another group, refers to both straight and branched chain radicals of up to ten carbons, and which comprise at least one carbon-carbon double bond.

The term "hydroxyalkyl" as employed herein, refers to both straight and branched chain alkyl radicals having a hydroxyl substituent. The hydroxyl substituent can be bound to any carbon of the alkyl chain. Non-limiting examples include —$CH_2OH$, —$CH_2CH_2OH$, —$CH_2CH(OH)CH_3$ and —$CH_2CH(OH)CH_2CH_3$. For example, the term "hydroxyalkyl" as employed herein can refer to a straight or branched chain radical comprising from one to four carbon atoms and having one or more hydroxyl substituents.

The term "alkoxy" as employed herein, by itself or as part of another group, refers to an alkyl group, as defined herein, appended to the parent molecular moiety through an oxygen atom. Non-limiting examples of alkoxy groups include methoxy, ethoxy, propoxy, 2-propoxy, butoxy, tert-butoxy, pentyloxy, and hexyloxy.

The term "cycloalkyl" as used herein refers to an alkyl group comprising a closed ring comprising from 3 to 8 carbon atoms. Non-limiting examples of cycloalkyl groups include cyclopropyl, cyclobutyl, cyclopentyl, cyclohexyl, cycloheptyl, (cyclohexyl)methyl, and (cyclohexyl)ethyl.

As used herein, the term "heterocyclyl," "heterocycloalkyl," or "heterocycle" refers to a saturated or partially saturated 3 to 7 membered monocyclic, or 7 to 10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and includes any bicyclic group in which any of the above-defined heterocyclic rings is fused to a benzene ring, and wherein the heterocyclic ring can be substituted on carbon or on a nitrogen atom if the resulting compound is stable. Non-limiting examples of common saturated or partially saturated heterocyclic groups include azetinyl, oxetanyl, tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "aryl" as employed herein by itself or as part of another group refers to monocyclic, bicyclic or tricyclic aromatic groups containing from 6 to 14 carbons in the ring. Common aryl groups include $C_{6-14}$ aryl, typically $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms. Example heteroaryl groups include thienyl (thiophenyl), benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl.

While there is no upper limit on the useful concentrations and dosages of a composition provided herein, lower effective concentrations and dosages will generally be sought for efficiency and economy. Non-limiting embodiments of effective amounts of the composition include those containing from about 10 nanograms per milliliter to about 100 micrograms per milliliter of a polynucleotide applied to a plant surface, or from about 10 milligrams per acre to about 100 grams per acre of polynucleotide applied to a field of plants, or from about 0.001 to about 0.1 microgram per milliliter of polynucleotide in an artificial diet for feeding the insect. Where compositions provided herein are topically applied to a plant, the concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using a composition containing a 25-mer polynucleotide is about 1 nanomole (nmol) of polynucleotide per plant, for example, from about 0.05 to 1 nmol polynucleotide per plant. Other embodiments for herbaceous plants include compositions containing about 0.05 to about 100 nmol, or about 0.1 to about 20 nmol, or about 1 nmol to about 10 nmol of polynucleotides per plant. In embodiments, a composition containing about 40 to about 50 nmol of a polynucleotide are applied. In embodiments, a composition containing about 0.5 nmol to about 2 nmol of a dsRNA is applied. In embodiments, a composition containing about 0.5 to about 2.0 milligrams per milliliter, or about 0.14 milligrams per milliliter of a dsRNA is applied. In embodiments, a composition containing about 0.5 to about 1.5 milligrams per milliliter of a dsRNA polynucleotide of about 50 to about 200 or more nucleotides is applied. In embodiments, a composition containing about 1 nmol to about 5 nmol of a dsRNA is applied to a plant. In embodiments, the composition as topically applied to the plant contains at least one polynucleotide at a concentration of about 0.01 to about 10 milligrams per milliliter, or about 0.05 to about 2 milligrams per milliliter, or about 0.1 to about 2 milligrams per milliliter. Very large plants, trees, or vines can require application of a composition containing correspondingly larger amounts of polynucleotides. When the composition contains multiple polynucleotides (e.g., multiple polynucleotides targeting the same gene), a composition containing lower concentrations of each polynucleotide. Non-limiting examples of effective treatment regimes include a treatment with a composition in order to provide between about 0.1 to about 1 nmol of polynucleotide per plant, or between about 1 nmol to about 10 nmol of polynucleotide per plant, or between about 10 nmol to about 100 nmol of polynucleotide per plant.

Disclosed herein are methods and compositions for delivering a polynucleotide to an invertebrate, for example an insect, nematode or mite, by providing a polynucleotide and a cationic polysaccharide to the invertebrate. A first aspect provides a composition including: (a) a cationic polysaccharide particle, and (b) a polynucleotide. In embodiments, the polynucleotide and the cationic polysaccharide particle are bound by electrostatic attraction to form a complex. In embodiments, the complex has at least one dimension that exceeds 200 nanometers. In embodiments, the complex has at least one dimension that exceeds 500 nanometers when hydrated. In some embodiments, the cationic polysaccharide is a cross-linked cationic polysaccharide.

Embodiments of the composition include those where the cross-linked cationic polysaccharide particle and a polynucleotide form a porous, hydrophilic particle. In embodiments, the complex is non-soluble in an aqueous solution. For example, the composition can be provided as an aqueous suspension of the cross-linked cationic polysaccharide/polynucleotide complex.

In embodiments, the cross-linked cationic polysaccharide is derived from a non-cationic, non-cross-linked polysaccharide, which can be linear or linear with branching/side groups. The non-cationic, non-cross-linked polysaccharide can be obtained from any usual source, including tubers, legumes, cereals, and grains. In embodiments, the non-cationic, non-cross-linked polysaccharide is starch or guar gum. In embodiments, the non-cationic, non-cross-linked polysaccharide is a starch selected from the group consisting of: corn starch, potato starch, rice starch, tapioca starch, and wheat starch. In embodiments, the cross-linked cationic polysaccharide is provided by reaction of a non-cross-linked polysaccharide with an alkylating agent, such as a diacid chloride. In some embodiments, the non-cross-linked polysaccharide is cationized by reaction with a cationic functionalization agent prior to cross-linking. In some embodiments, a cross-linked, non-cationic, polysaccharide is cationized by reaction with a cationic functionalization agent. In embodiments, the cross-linked cationic polysaccharide is provided by cross-linking a commercially available cationic polysaccharide. In embodiments, the cross-linked cationic polysaccharide is provided as particles which are not soluble in water, or are not substantially soluble in water; compositions containing these can be provided as a dry composition, or as a liquid or aqueous suspension of the particles.

In embodiments of the cross-linked cationic polysaccharide/polynucleotide composition, the cross-linked cationic polysaccharide comprises one or more cationic functional groups. Examples of cationic functional groups include amines and ammonium cations, such as a primary amine, a secondary amine, a tertiary amine, and a quaternary ammonium cation. In embodiments where the cross-linked cationic polysaccharide/polynucleotide composition is provided as an aqueous suspension, the one or more cationic functional groups is positively charged at the pH of the aqueous suspension. In some embodiments, the cross-linked cationic polysaccharide comprises one or more amines or ammonium cations selected from the group consisting of optionally substituted amine, nitrogen-containing heterocyclyl, quaternary ammonium, and nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the cross-linked cationic polysaccharide comprises one or more amines or ammonium cations selected from the group consisting of —$NH_2$, —$NHR^1$, —$NR^1R^2$, —$NR^1R^2R^3$ and, —$N^+R^1R^2R^3R^4$, wherein $R^1$, $R^2$, $R^3$, and $R^4$ are each independently alkyl, each of which may be optionally independently substituted with one or more of hydroxyl, alkyl, alkenyl, alkoxy, amino, aryl, heterocyclyl, or heteroaryl. In some embodiments $R^1$, $R^2$, $R^3$, and $R^4$ can be each independently $C_1$-$C_6$ alkyl, each of which may be optionally independently substituted with one or more of hydroxyl, $C_1$-$C_6$ alkyl, $C_1$-$C_6$ alkenyl, $C_1$-$C_6$ alkoxy, amino, aryl, heterocyclyl, or heteroaryl. Non-limiting examples of $C_1$-$C_6$ alkyl groups include methyl, ethyl, propyl, isopropyl, butyl, sec-butyl, tert-butyl, 3-pentyl, and hexyl groups. In some embodiments, the $C_1$-$C_6$ alkyl is selected from the group consisting of methyl, ethyl, propyl, butyl, 3-pentyl and hexyl, each of which may be optionally independently substituted with one or more of hydroxyl. In some embodiments, the cross-linked cationic polysaccharide comprises a quaternary ammonium cation comprising —$N^+R^1R^2R^3R^4$, wherein $R^1$, $R^2$, $R^3$, and $R^4$ are as defined above. In some embodiments, the quaternary ammonium cation of —$N^+R^1R^2R^3R^4$ can be a hydroxyalkyl-trialkylammonium cation, wherein $R^1$, $R^2$, and $R^3$ are the same alkyl and $R^4$ is hydroxyalkyl (e. g., a 2-hydroxypropyltrimethylammonium cation).

In some embodiments the cationic agents used in the synthesis of cross-linked cationic polysaccharides comprises an ammonium group. Suitable cationic agents comprising an ammonium group include, for example, glycidyltrimethylammonium chloride (GTAC) (also known as 2,3-epoxypropyl-N,N,N-trimethylammonium chloride), 3-chloro-2-hydroxypropyl-N,N,N-trimethylammonium chloride, 3-chloro-2-hydroxypropyl-N,N,N-dimethylethanolammonium chloride, 1,3-bis-(3-chloro-2-hydroxypropyl-N,N-dimethylammonium)-N-propane dichloride. Examples of cationic functionalization of polysaccharides comprising starches and guar gums are provided in the working Examples. In an embodiment, the alkylating agent is glycidyl trimethylammonium chloride (GTAC); in embodiments, GTAC can be present in the reaction in an amount of from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked polysaccharide. The content of a cationic functional group per monomeric unit represents the degree of quaternization of the above-prepared cross-linked cationic polysaccharides. The nitrogen content of an elemental analysis (i.e., C, H, N analyses) can be used to calculate the content of a cationic functional group per monomeric unit. In some embodiments, the content of a cationic functional group per monomeric unit of the cross-linked cationic polysaccharide is from about 5% to about 50%, from about 5% to about 40%, from about 5% to about 30%, from about 5% to about 20%, from about 10% to about 50%, from about 10% to about 40%, from about 10% to about 30%, or from about 10% to about 20%.

Covalent cross-linking of polysaccharides such as starches and guars is commonly carried out with cross-linking reagents such as aldehydes (e. g., formaldehyde or glutaraldehyde); dicarboxylic acids (e. g., maleic acid); dialdehydes (e. g., glyoxal); epoxides (e. g., diglycidyl ether, diglycidyl PEG, vinylcyclohexene dioxide, bisphenol A diglycidyl ether, 1,4-butanediol diglycidyl ether, and epichlorohydrin), divinyl compounds, dihalogen compounds, halohydrins, diacylchlorides (e. g., adipoyl chloride, phthaloyl chloride, and oxalyl chloride), phosphorus oxychloride, dihydrazides (bis-hydrazides), alkoxyamines, diisocyanates, carbodiimides (e. g., 1-ethyl-(dimethylaminopropyl)carbodiimide (EDC)), and ethylene glycols (e. g., polyethylene glycol). Cross-linking can include one or more reaction steps, for example, intermediate reactions such as oxidation (e. g., with periodic acid (or periodate) to convert vicinal diols to aldehydes which are conveniently cross-linked). The cross-linking can include both covalent cross-linking and non-covalent (electrostatic or ionic) interactions. One of skill in the art would be familiar with readily available cross-linking methods, such as those described in "Bioconjugate Techniques, 3rd Edition" (2013), Greg T. Hermanson, Academic Press, Waltham, Mass., ISBN-10: 0123822394; ISBN-13: 9780123822390.

Examples of cross-linking of polysaccharides such as starches and guar gums are provided in the working Examples. In an embodiment, the cross-linked polysaccharide is provided by reaction of a non-cross-linked polysaccharide with diacid chlorides of dicarboxylic acids or with diglycidyl ethers. In embodiments, the cross-linked polysaccharide is provided by reaction of a non-cross-linked polysaccharide with phosphoryl chloride ($POCl_3$), diglycidyl polyethylene glycol (PEG), diglycidyl bisphenol A, and diglycidyl 1,4-butanediol, oxalyl chloride, phthaloyl chloride, and adipoyl chloride. In embodiments, a cross-linked cationic polysaccharide is provided by reaction of a non-cross-linked polysaccharide with glycidyl trimethylammonium chloride (GTAC) and with phosphoryl chloride ($POCl_3$); in embodiments, the $POCl_3$ can be present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 wt. % to about 4 wt. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked polysaccharide. In specific embodiments of the composition comprising a cross-linked cationic polysaccharide and a polynucleotide, wherein the cross-linked cationic polysaccharide is provided by reaction of a non-cross-linked polysaccharide with glycidyl trimethylammonium chloride (GTAC) and with phosphoryl chloride ($POCl_3$), and the polynucleotide comprises RNA (such as a double-stranded RNA). In a specific embodiment of the composition comprising a cross-linked cationic polysaccharide and a polynucleotide, wherein the cross-linked cationic polysaccharide is provided by reaction of a non-cross-linked cationic polysaccharide with phosphoryl chloride ($POCl_3$) and the polynucleotide comprises RNA; and wherein the $POCl_3$ is present in the reaction in an amount of from about 1 wt. % to about 5 wt. %, from about 2 wt. % to about 5 wt. %, from about 3 wt. % to about 5 wt. %, from about 4 wt. % to about 5 wt. %, from about 1 w.t. % to about 4 w.t. %, from about 2 wt. % to about 4 wt. %, from about 3 wt. % to about 4 wt. %, from about 1 wt. % to about 3 wt. %, from about 2 wt. % to about 3 wt. %, or from about 1 wt. % to about 2 wt. %, based on the non-cross-linked cationic polysaccharide.

In embodiments of the cross-linked cationic polysaccharide/polynucleotide composition, the cross-linked cationic polysaccharide comprises a glucan, a galactan, a galactomannan, a derivative thereof, and any combination thereof. Examples of suitable glucans include starch, amylose, amylopectin, dextran, maltodextrin, and cellulose. Examples of suitable galactans include agar. Examples of suitable galactomannans include guar gum, locust bean gum, tara gum, and fenugreek gum. Examples of suitable derivatives of glucans or galacans includes chitin, chitosan, and carrageenan. In embodiments of the cross-linked cationic polysaccharide/polynucleotide composition, the cross-linked cationic polysaccharide comprises a monomeric unit selected from the group consisting of glucose, galactose, fructose, mannose, glucosamine, N-acetylglucosamine, galactosamine, a derivative thereof, and combinations thereof. For example, chitin comprises the monomeric unit of N-acetylglucosamine; chitosan comprises the monomeric units of N-acetylglucosamine and glucosamine; and carrageenan comprises the monomeric units of glactose and a derivative of glactose (i.e., 3,6 anhydrogalactose). In embodiments of the cross-linked cationic polysaccharide/polynucleotide composition, the ratio (w/w) of cross-linked cationic polysaccharide to polynucleotide is 0.2:1 to 50:1.

Embodiments of the composition comprising a cross-linked cationic polysaccharide and a polynucleotide, further comprises one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant. In some embodiments, preparation of the composition comprising a cross-linked cationic polysaccharide and a polynucleotide includes the use of materials such as water or non-aqueous liquids or solvents, a chelator, a buffer, a filler, a binder, a hardener, a sticking agent, a pH modifier, a dispersant, a non-ionic surfactant, a zwitterionic surfactant, a silicate, or a defoamer, even if the final formulation does not contain these materials. In embodiments, the composition is formulated to include one or more non-polynucleotide pesticides (such as a non-polynucleotide insecticide, herbicide, or fungicide, or combinations thereof); examples of non-polynucleotide pesticides include a patatin, a plant lectin, a phytoecdysteroid, a *Bacillus thuringiensis* insecticidal protein, a Xenorhabdus insecticidal protein, a *Photorhabdus* insecticidal protein, a *Bacillus* laterosporous insecticidal protein, and a *Bacillus sphaericus* insecticidal protein. In embodiments, one or more non-ionic surfactants are added to the formulation to aid in disintegration and improve spray quality, while avoiding the introduction of ions which could interact with the polynucleotide or with the cross-linked cationic polysaccharide. Examples of suitable non-ionic surfactants include castor oil ethoxylate (e. g., Emulpon CO-550 from Akzo Nobel, 13295 Lakefront Dr, Earth City, Mo. 63045), or block copolymers of ethylene oxide and propylene oxide ("EO-PO copolymers") such as Pluronic F108, an EO-PO copolymer from BASF (equivalent to poly(ethylene glycol)-block-poly(propylene glycol)-block-poly(ethylene glycol), average $M_n$~14,600, Aldrich catalogue number 542342, CAS Number 9003-11-6, Sigma-Aldrich). Non-limiting embodiments of dispersants include lignosulfonates, for example, sodium lignosulphonates sold as Ultrazine NA or Ufoxane Ultra CA (Borregaard LignoTech) and Reax 907 (Mead Westvaco). An example of a material that acts as a filler or hardener is kaolin, a type of clay which does not swell in water. An example of a material that acts as a hardener and improves disintegration is fumed silica (e. g., Aerosil 200), which also absorbs water, toughening solid formulations prior to extrusion and drying. In embodiments, disintegrants are used accelerate disintegration; examples of suitable disintegrants include urea and sorbitol. In embodiments, modified polysaccharides such as low-molecular weight carboxymethyl cellulose (e. g., Finnfix 2) can serve both as a disintegrant and a binder, strengthening wet formulations. In some embodiments the formulation includes other excipients such as corn syrup, sugar syrup, sugar solid, sugar semi-solids, pollen, soy protein, pollen, protein mixtures, and any combination thereof. In embodiments the formulation includes a biocide such as dichlorophen or benzyl alcohol hemiformal based compounds, benzothiazolinones, and rhamnolipids. Non-limiting examples of commercially available biocidal agents include ACTICIDE, Proxel GXL (1,2-benzisothiazolin-3-one), and Zonix. In embodiments the formulation includes a chelator such as citric acid, salts of ethylenediamine tetracetic acid (EDTA) and the Dequest series of phosphonate chelators (available from Italmatch). In embodiments the formulation includes a surfactant such as silicone surfactants, alkyl polyglycosides, ethoxylated fatty acids and alcohols, ethoxylated sorbitan esters, alkyl betaine ethoxylates, and mixtures thereof. Non-limiting examples of commercially available surfactants include SILWET L-77, AGNIQUE PG, TWEEN and ALKEST. In embodiments the formulation includes a defoamer, such as a silicone defoamer. Non-limiting examples of commercially available defoamers include AGNIQUE DFM 111S. In embodiments the formulation includes a photoprotectant such as an aromatic disulfonate. Various embodiments of such compositions including these additional components, or employing these additional components during preparation, are described in the working Examples.

A related aspect provides a method of increasing the stability of a polynucleotide comprising: combining a cross-linked cationic polysaccharide particle with a polynucleotide to form a particle. In embodiments, the particle has at least one dimension that exceeds 200 nanometers. In embodiments, the particle has at least one dimension that exceeds 500 nanometers when hydrated. Another aspect provides a method of improving the rainfastness of a polynucleotide, comprising combining a polynucleotide with a cross-linked cationic polysaccharide particle to form a cationic, hydrophilic complex. A further aspect provides a method of improving the photostability of a polynucleotide, comprising combining a polynucleotide with a cross-linked cationic polysaccharide particle to form a cationic, hydrophilic complex; in embodiments, the cationic, hydrophilic complex further comprises a photoprotectant. These and related aspects are illustrated in the working Examples.

Several embodiments relate to a composition comprising a cationic polysaccharide, a polynucleotide and a silicate. In some embodiments, the silicate binds to the cationic polysaccharide/polynucleotide complex, and the resulting particulates are conveniently recoverable by filtration or sedimentation, which permits concentration and purification of the cationic polysaccharide/polynucleotide complex. In some embodiments, the polynucleotide is provided in a bacterial lysate. In some embodiments, the silicate binds to the cationic polysaccharide/polynucleotide complex, and the resulting particulates are separable from endotoxin and other material contained in the bacterial lysate. Examples of silicates useful in these compositions include silicates selected from the group consisting of silicon dioxide, aluminum silicate, and magnesium silicate. Embodiments include those where the silicate is a clay; specific embodiments include those where the silicate is selected from the group consisting of montmorillonite, kaolinite, bentonite clay, and kaolin clay. In some embodiments, a method of purifying a cationic polysaccharide/polynucleotide complex by addition of a silicate is provided.

Several embodiments disclosed herein relate to methods and compositions for delivering a polynucleotide to an invertebrate, for example an insect or mite, by providing a polynucleotide and a cationic guar gum to the invertebrate. A first aspect provides a composition including: (a) a cationic guar gum, and (b) a polynucleotide. In embodiments, the polynucleotide and the cationic guar gum are bound by electrostatic attraction to form a complex. In various embodiments, the cationic guar gum is (a) a linear cationic guar gum, (b) a cross-linked cationic guar gum, or (c) a mixture of linear and cross-linked cationic guar gums. In some embodiments, the cationic guar gum is a particle. In some embodiments, the complex has at least one dimension that exceeds 200 nanometers. In embodiments, the complex has at least one dimension that exceeds 1 micrometer. In embodiments, the complex has at least one dimension that exceeds 500 nanometers when hydrated. Related, analogous embodiments include those where the composition includes a cationic galactomannan other than guar gum (such as a cationic locust bean gum, tara gum, or fenugreek gum), and a polynucleotide.

In some embodiments, the cationic guar gum/polynucleotide complex is a porous, hydrophilic particle. In embodiments, the cationic guar gum/polynucleotide complex is non-soluble in an aqueous solution. In embodiments, the composition including the cationic guar gum/polynucleotide complex is provided as an aqueous suspension or as a water-dispersible granule. Examples of formulations including the cationic guar gum/polynucleotide compositions are provided in the working Examples.

Several embodiments relate to a composition comprising a cationic guar gum and a polynucleotide and a silicate. In some embodiments, the silicate binds to the cationic guar gum/polynucleotide complex, and the resulting particulates are conveniently recoverable by filtration or sedimentation, which permits concentration and purification of the cationic guar gum/polynucleotide complex. In some embodiments, the polynucleotide is provided in a bacterial lysate. In some embodiments, the silicate binds to the cationic guar gum/polynucleotide complex, and the resulting particulates are separable from endotoxin and other material contained in the bacterial lysate. Examples of silicates useful in these compositions include silicates selected from the group consisting of silicon dioxide, aluminum silicate, and magnesium silicate. Embodiments include those where the silicate is a clay; specific embodiments include those where the silicate is selected from the group consisting of montmorillonite, kaolinite, bentonite clay, and kaolin clay. In some embodiments, a method of purifying a cationic guar gum/polynucleotide complex by addition of a silicate is provided. Various embodiments of cationic guar gum/polynucleotide compositions that further include a silicate such a clay are described in the working Examples.

Embodiments of the composition include a cationic guar gum and a polynucleotide, and further include one or more of water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, and a photo-protectant. In some embodiments, preparation of the composition including a cationic guar gum and a polynucleotide includes the use of materials such as water or non-aqueous liquids or solvents, a chelator, a buffer, a filler, a binder, a hardener, a sticking agent, a pH modifier, a dispersant, a non-ionic surfactant, a zwitterionic surfactant, or a defoamer, even if the final formulation does not contain these materials. In embodiments, the composition is formulated to include one or more non-polynucleotide pesticides (such as a non-polynucleotide insecticide, herbicide, or fungicide, or combinations thereof); examples of non-polynucleotide pesticides include a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein. In embodiments, one or more non-ionic surfactants are added to the formulation to aid in disintegration and improve spray quality, while avoiding the introduction of ions which could interact with the polynucleotide or with the cationic guar gum. Examples of suitable non-ionic surfactants include castor oil ethoxylate (e. g., Emulpon CO-550), or block copolymers of ethylene oxide and propylene oxide ("EO-PO copolymers") such as Pluronic F108, an EO-PO copolymer from BASF (equivalent to poly(ethylene glycol)-block-poly(propylene glycol)-block-poly(ethylene glycol), average $M_n$~14,600). Non-limiting embodiments of dispersants include lignosulfonates, for example, sodium lignosulphonates sold as Ultrazine NA or Ufoxane Ultra CA and Reax 907. An example of a material that acts as a filler or hardener is kaolin, a type of clay which does not swell in water. An example of a material that acts as a hardener and improves disintegration is fumed silica (e. g., Aerosil 200, CAS number 112945-52-5 or 7631-86-9, Evonik Corporation, 299 Jefferson Road, Parsippany, N.Y. 07054), which also absorbs water, toughening solid formulations prior to extrusion and drying. In embodiments, disintegrants are used accelerate disintegration; examples of suitable disintegrants include urea and sorbitol. In embodiments, modified polysaccharides such as low-molecular weight carboxymethyl cellulose (e. g., Finnfix 2) can serve both as a disintegrant and a binder, strengthening wet formulations. In some embodiments the formulation includes other excipients such as corn syrup, sugar syrup, sugar solid, sugar semi-solids, pollen, soy protein, pollen, protein mixtures, and any combination thereof. In embodiments the formulation includes a biocide such as dichlorophen or benzyl alcohol hemiformal based compounds, benzothiazolinones, and rhamnolipids. Non-limiting examples of commercially available biocidal agents include ACTICIDE (available from THOR), Proxel GXL (1,2-benzisothiazolin-3-one, available from Arch Chemical), and Zonix (available from Jeneil). In embodiments the formulation includes a chelator such as citric acid, salts of ethylenediamine tetracetic acid (EDTA) and the Dequest series of phosphonate chelators (available from Italmatch). In embodiments the formulation includes a surfactant such as silicone surfactants, alkyl polyglycosides, ethoxylated fatty acids and alcohols, ethoxylated sorbitan esters, alkyl betaine ethoxylates, and mixtures thereof. Non-limiting examples of commercially available surfactants include SILWET L-77, AGNIQUE PG, TWEEN and ALKEST. In embodiments the formulation includes a defoamer, such as a silicone defoamer. Non-limiting examples of commercially available defoamers include AGNIQUE DFM 111S. In embodiments the formulation includes a photoprotectant such as an aromatic disulfonate. Various embodiments of such compositions including these additional components, or employing these additional components during preparation, are described in the working Examples.

Specific embodiments of the composition include those wherein: (a) the polynucleotide includes an RNA molecule and the cationic guar gum includes a linear cationic guar gum; (b) the polynucleotide includes a dsRNA and the cationic guar gum includes a linear cationic guar gum; (c) the polynucleotide includes an RNA molecule and the cationic guar gum includes a cross-linked cationic guar gum; or (d) the polynucleotide includes a dsRNA and the cationic guar gum includes a cross-linked cationic guar gum.

In embodiments, the cross-linked cationic guar gum is derived from a non-cationic, non-cross-linked guar gum. Related embodiments include those where instead of guar gum, another galactomannan is used, such as locust bean gum, tara gum, or fenugreek gum. In embodiments, the guar gum is partially hydrolyzed; partial hydrolysis reduces the molecular weight of guar gum to improve its solubility. Partially hydrolyzed guar gum can be produced by either enzymatic or acid hydrolysis. Enzymatically-hydrolyzed guar gum is commercially available under the trade name Sunfiber® from Taiyo International. Alternatively, commercial guar gum can be hydrolyzed with acid in a non-aqueous solvent as described in the Examples and in Kumar, S.; Chandra, S.; Mathur, V.; Mathur, N. K., "Bead Form of Guaran Gel for Chromatographic Column Packing," Reactive Polymers, 1993, 21, 141-3.

In embodiments, a cationic, cross-linked guar gum is provided by reaction of a non-cross-linked guar gum with an alkylating agent. In some embodiments, the non-cross-linked guar gum is cationized by reaction with a cationic functionalization agent prior to cross-linking. In some embodiments, non-cationic cross-linked guar gum is cationized by reaction with a cationic functionalization agent. In embodiments, the cross-linked cationic guar gum is provided by cross-linking a commercially available cationic guar gum; examples of commercially available cationic guar gum include various cationic guars sold under the trade name Jaguar® (available from Solvay USA Inc.) as well as various cationic guars available from Ashland (trade names N-Hance® and Aquacat®; Ashland, Inc. Dow (guar hydroxypropyltrimonium chloride sold under the trade name EcoSmooth 120E), Lamberti (cationic guars sold under the trade names Lamfix® and ESAFLOR), and BASF (guar hydroxypropyltrimonium chlorides sold under the trade names Dehyquart® Guar HP, Dehyquart® Guar N, and Dehyquart® Guar TC).

In embodiments of the cationic guar gum/polynucleotide composition, the cationic guar gum comprises one or more cationic functional groups. Examples of cationic functional groups include amines and ammonium cations, such as a primary amine, a secondary amine, a tertiary amine, and a quaternary ammonium cation. In embodiments where the cationic guar gum/polynucleotide composition is provided as an aqueous suspension, the one or more cationic functional groups is positively charged at the pH of the aqueous suspension. In some embodiments, the cationic guar comprises one or more amines or ammonium cations selected from the group consisting of optionally substituted amine, nitrogen-containing heterocyclyl, quaternary ammonium, and nitrogen-containing heteroaryl, each of which may be optionally independently substituted with one or more of hydroxyl, alkyl, cycloalkyl, alkenyl, alkoxy, amino, aryl, heterocyclyl, or heteroaryl. In some embodiments, the cationic guar comprises one or more amines or ammonium cations selected from the group consisting of —NH2, —NHR1, —NR1R2, —NR1R2R3, and —N+R1R2R3R4, wherein R1, R2, R3, and R4 are each independently alkyl, each of which may be optionally independently substituted with one or more of hydroxyl, alkyl, alkenyl, alkoxy, amino, aryl, heterocyclyl, or heteroaryl. In some embodiments R1, R2, R3, and R4 can be each independently C1-C6 alkyl, each of which may be optionally independently substituted with one or more of hydroxyl, C1-C6 alkyl, C1-C6 alkenyl, C1-C6 alkoxy, amino, aryl, heterocyclyl, or heteroaryl. Non-limiting examples of C1-C6 alkyl groups include methyl, ethyl, propyl, isopropyl, butyl, sec-butyl, tert-butyl, 3-pentyl, and hexyl groups. In some embodiments, the C1-C6 alkyl is selected from the group consisting of methyl, ethyl, propyl, butyl, 3-pentyl and hexyl, each of which may be optionally independently substituted with one or more of hydroxyl. In some embodiments, the cationic guar comprises a quaternary ammonium cation comprising —N+R1R2R3R4, wherein R1, R2, R3, and R4 are as defined above. In some embodiments, the quaternary ammonium cation of —N+R1R2R3R4 can be a hydroxyalkyl-trialkylammonium cation, wherein R1, R2, and R3 are the same alkyl and R4 is hydroxyalkyl (e. g., a 2-hydroxypropyltrimethylammonium cation).

In embodiments the cationic agents used in the synthesis of cross-linked cationic guar gums include an ammonium group. Suitable cationic agents including an ammonium group include, for example, glycidyltrimethylammonium chloride (GTAC), 2,3-epoxypropyl-N,N,N-trimethylammonium chloride, 3-chloro-2-hydroxypropyl-N,N,N-trimethylammonium chloride, 3-chloro-2-hydroxypropyl-N,N,N-dimethylethanolammonium chloride, 2,3-epoxypropyl-N,N,N-trimethylammonium chloride, 1,3-bis-(3-chloro-2-hydroxypropyl-N,N-dimethylammonium)-N-propane dichloride. Examples of cationic functionalization of guar gums are provided in the working Examples. In an embodiment, the functionalizing agent is glycidyl trimethylammonium chloride (GTAC); in embodiments, the ratio (w/w) of GTAC to non-cross-linked guar gum in the reaction is from about 1 wt. % to about 70 wt. %, from about 2 wt. % to about 70 wt. %, from about 5 wt. % to about 70 wt. %, from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 20 wt. % to about 70 wt. %, from about 20 wt. % to about 60 wt. %, from about 30 wt. % to about 70 wt. %, or from about 40 wt. % to about 60 wt. %, based on the non-cross-linked guar. The content of a cationic functional group per monomeric unit represents the degree of quaternization of the above-prepared cationic guar. The nitrogen content of an elemental analysis (i.e., C, H, N analyses) can be used to calculate the content of a cationic functional group per monomeric unit. In some embodiments, the content of a cationic functional group per monomeric unit of the cationic guar is from about 5% to about 50%, from about 5% to about 40%, from about 5% to about 30%, from about 5% to about 20%, from about 10% to about 50%, from about 10% to about 40%, from about 10% to about 30%, or from about 10% to about 20%.

Covalent cross-linking of guar gum is carried out with cross-linking reagents such as aldehydes (e. g., formaldehyde or glutaraldehyde); dicarboxylic acids (e. g., maleic acid); dialdehydes (e. g., glyoxal); epoxides (e. g., diglycidyl ether, diglycidyl PEG, vinylcyclohexene dioxide, bisphenol A diglycidyl ether, 1,4-butanediol diglycidyl ether, and epichlorohydrin), divinyl compounds, dihalogen compounds, halohydrins, diacylchlorides (e. g., adipoyl chloride, phthaloyl chloride, and oxalyl chloride), phosphorus oxychloride, dihydrazides (bis-hydrazides), alkoxyamines, diisocyanates, carbodiimides (e. g., 1-ethyl-(dimethylaminopropyl)carbodiimide (EDC)), and ethylene glycols (e. g., polyethylene glycol). Cross-linking can include one or more reaction steps, and in some embodiments includes intermediate reactions such as oxidation (e. g., with periodic acid (or periodate) to convert vicinal diols to aldehydes which are conveniently cross-linked). In embodiments, cross-linking includes both covalent cross-linking and non-covalent (electrostatic or ionic) interactions. One of skill in the art would be familiar with readily available cross-linking methods, such as those described in "Bioconjugate Techniques, 3rd Edition" (2013), Greg T. Hermanson, Academic Press, Waltham, Mass., ISBN-10: 0123822394; ISBN-13: 9780123822390.

Non-limiting examples of cross-linking of guar gums are provided in the working Examples. In an embodiment, the cross-linked guar gum is provided by reaction of a non-cross-linked guar gum with diacid chlorides of dicarboxylic acids or with diglycidyl ethers. In embodiments, the cross-linked guar gum is provided by reaction of a non-cross-linked guar gum with phosphoryl chloride ($POCl_3$), diglycidyl polyethylene glycol (PEG), diglycidyl bisphenol A, and diglycidyl 1,4-butanediol, oxalyl chloride, phthaloyl chloride, and adipoyl chloride. In embodiments, a cross-linked cationic guar gum is provided by reaction of a non-cross-linked guar gum with glycidyl trimethylammonium chloride (GTAC) and with phosphoryl chloride ($POCl_3$); in embodiments, the ratio (w/w) of the $POCl_3$ to non-cross-linked guar gum in the reaction is from about 1% to about 5%, from about 2% to about 5%, from about 3% to about 5%, from about 4% to about 5%, from about 1% to about 4%, from about 2% to about 4%, from about 3% to about 4%, from about 1% to about 3%, from about 2% to about 3%, or from about 1% to about 2%. In specific embodiments of the composition, the cross-linked cationic guar gum is provided by reaction of a non-cross-linked guar gum with glycidyl trimethylammonium chloride (GTAC) and with phosphoryl chloride ($POCl_3$), and the polynucleotide includes RNA (such as a double-stranded RNA). In a specific embodiment of the composition, the cross-linked cationic guar gum is provided by reaction of a non-cross-linked cationic guar gum with phosphoryl chloride ($POCl_3$), the polynucleotide includes RNA, and the ratio (w/w) of the $POCl_3$ to non-cross-linked guar gum in the reaction is from about 1% to about 5%, from about 2% to about 5%, from about 3% to about 5%, from about 4% to about 5%, from about 1% to about 4%, from about 2% to about 4%, from about 3% to about 4%, from about 1% to about 3%, from about 2% to about 3%, or from about 1% to about 2%.

In embodiments of the cationic guar gum/polynucleotide composition, the cationic guar gum is a linear or non-cross-linked cationic guar gum. In other embodiments, the cationic guar gum is a cross-linked cationic guar gum. In embodiments of the cationic guar gum/polynucleotide composition, the cationic guar gum is a cross-linked cationic guar gum provided by reaction of a linear cationic guar gum with one or more cross-linking agents. In embodiments of the cationic guar gum/polynucleotide composition, the cationic guar gum is a cross-linked cationic guar gum provided by reaction of a linear cationic guar gum with one or more cross-linking agents selected from the group consisting of diacid chlorides of dicarboxylic acids, diglycidyl ethers, phosphoryl chloride (POCl3), diglycidyl polyethylene glycol (PEG), diglycidyl bisphenol A, diglycidyl 1,4-butanediol, oxalyl chloride, phthaloyl chloride, and adipoyl chloride.

Specific embodiments of the cationic guar gum/polynucleotide composition include those wherein the cationic guar gum is one or more selected from the group consisting of: (a) guar gum, hydroxypropyltrimonium chloride, (b) guar gum, 2-hydroxypropyl 2-hydroxy-3-(trimethylammonio)propyl ether, chloride, (c) hydroxypropyl cationic guar, mol. wt. approximately 2 million Dalton, (d) cationic guar, degree of substitution approximately 12%, mol. wt. approximately 0.5 million Dalton, and (e) Lamfix 11; such embodiments include those wherein the polynucleotide is single-stranded DNA, double-stranded DNA, single-stranded RNA, double-stranded RNA, or any combination of these. In various embodiments of the cationic guar gum/polynucleotide composition, the ratio of cationic guar gum to polynucleotide is 0.2:1 to 50:1 based on weight.

The polynucleotides described herein can be a single molecule that self-hybridizes to form an at least partially double-stranded polynucleotide, for example, a single RNA molecule that includes self-complementary regions that base-pair to form an at least partially double-stranded polynucleotide (e. g., an RNA "hairpin").

A related aspect provides a method of increasing the stability of a polynucleotide including: combining a cationic guar gum with a polynucleotide to form a complex. In embodiments of this method, the cationic guar gum/polynucleotide complex forms a particle. Another aspect provides a method of improving the rainfastness of a polynucleotide, including: combining a polynucleotide with a cationic guar gum to form a cationic, hydrophilic complex. Another aspect provides a method of improving the photostability of a polynucleotide, including: combining a polynucleotide with a cationic guar gum to form a cationic, hydrophilic complex; in embodiments, the cationic, hydrophilic complex further includes a photoprotectant.

Polynucleotides such as dsRNA are typically prepared as aqueous solutions. Methods of preparing solid formulations from such aqueous solutions are useful. Lyophilization is one suitable technique. Disclosed herein is an economical and convenient alternative to lyophilization for preparing solid formulations including a cationic guar gum and a polynucleotide. Combining a solution of a polynucleotide such as a dsRNA with a solution of a cationic guar gum yields a solution or suspension of a cationic guar gum/polynucleotide complex, which can be used to prepare a dry formulation, such as a powder or a water-dispersible granule, which concentrates the polynucleotide in a dry form which is resistant to degradation. In addition to improved polynucleotide loading and stability, preparation of the solid formulation enables separation of the polynucleotide from impurities in the parent solution. Rehydration, dissolution, or resuspension of the dry formulation into a liquid, sprayable formulation allows addition of other components to improve rehydration, disintegration, dissolution, or resuspension of the dry formulation as well as improving spray quality, rainfastness, and stability of the sprayable formulation.

In embodiments, it is desirable to later dissociate or displace the cationic guar gum/polynucleotide complex from the silicate. This is achieved by treating the cationic guar gum/polynucleotide/silicate mixture with a displacement agent. In some embodiments, the silicate is a montmorillonite clay. Thus, disclosed herein is a further aspect providing a method of preparing a purified polynucleotide/cationic guar gum composition including addition of a displacement agent to a composition including a polynucleotide/cationic guar gum complex and a silicate, whereby the polynucleotide/cationic guar gum complex is displaced from the silicate, thereby providing a purified polynucleotide/cationic guar gum composition. Embodiments of this method include those wherein the displacement agent includes a cationic amine surfactant (e. g., a protonated tertiary amine surfactant), a tertiary amine, an ammonium salt, or a water-soluble polar polymer. Specific embodiments of this method include those wherein the displacement agent is polyvinylpyrrolidone, dimethyldistearylammonium chloride, or gluconic acid salts of tertiary amine surfactants (e. g., Armeen DMOD or Ethomeen® C/15, available from Akzo Nobel).

In several embodiments, the methods and compositions described herein provide one or more polynucleotides that act as a pest control agent. The compositions described herein provide in part a delivery system for the delivery of the pest control agents to pests through their exposure to a diet containing the pest control agent. The polynucleotides described herein as pest control agents can be single-stranded (ss) or double-stranded (ds). "Double-stranded" refers to the base-pairing that occurs between sufficiently complementary, anti-parallel nucleic acid strands to form a double-stranded nucleic acid structure, generally under physiologically relevant conditions. Embodiments include those wherein the polynucleotide is selected from the group consisting of sense single-stranded DNA (ssDNA), sense single-stranded RNA (ssRNA), double-stranded RNA (dsRNA), double-stranded DNA (dsDNA), a double-stranded DNA/RNA hybrid, anti-sense ssDNA, or anti-sense ssRNA; a mixture of polynucleotides of any of these types can be used. In some embodiments, the polynucleotide pest control agent comprises a dsRNA molecule. In some embodiments, the polynucleotide molecule, such as a dsRNA, comprises one or more segments comprising 18 or more contiguous nucleotides, for example 21 or more contiguous nucleotides, having 95% to about 100% (e. g., about 95%, about 96%, about 97%, about 98%, about 99%, or about 100%) complementarity with a fragment of a target gene of a pest. Several embodiments relate to a dsRNA having a length greater than that which is typical of naturally occurring regulatory small RNAs (such as endogenously produced siRNAs and mature miRNAs), i.e., the dsRNA is at least about 30 contiguous base-pairs in length. In some embodiments, the dsRNA has a length of between about 50 to about 500 base-pairs. In some embodiments, the dsRNA has a length of about 30, 40, 50, 60, 70, 80. 90. 100, 150, 200, 250, 300, 350, 400, 450, 500, 550, 600, 650, 700, 800, 850, 900, 950, 1,000 or more base-pairs. In some embodiments, the dsRNA is formed from two separate, essentially complementary strands (e. g., where each strand is separately provided, or where each strand is encoded on a separate DNA molecule, or where the two strands are encoded on separate sections of a DNA and are separately transcribed or made separate, for example, by the action of a recombinase or nuclease), wherein at least one RNA strand includes a sequence of about 95% to about 100% (e. g., about 95%, about 96%, about 97%, about 98%, about 99%, or about 100%) identity or complementarity with a sequence of a target gene of a pest. In some embodiments, the dsRNA is blunt-ended, e. g., two separate, equal-length strands of RNA which form the dsRNA through intermolecular hybridisation. In some embodiments, the dsRNA has an overhang at one or both ends (termini), e. g., two separate, unequal-length strands of RNA which form the dsRNA through intermolecular hybridisation; the overhang can be a single nucleotide or 2, 3, 4, 5, 6, or more nucleotides, and can be located on the 5' end or on the 3' end of a strand. In some embodiments, the dsRNA includes at least one stem-loop, e. g., a single RNA molecule that forms a dsRNA with a "hairpin" secondary structure through intramolecular hybridization. In some embodiments, the dsRNA is formed from a single self-hybridizing hairpin transcript. In some embodiments, the dsRNA includes multiple stem-loops, with or without spacer nucleotides between each stem-loop. The dsRNA can be chemically synthesized (e. g., by in vitro transcription, such as transcription using a T7 polymerase or other polymerase), or can be produced by expression in a microorganism, by expression in a plant cell, or by microbial fermentation. The dsRNA can be chemically modified, e. g., to improve stability, ease of formulation, or efficacy. In some embodiments, the dsRNA molecule is provided in a microbial cell that expresses dsRNA, or in a microbial fermentation product. In some embodiments, the polynucleotide can include components other than standard ribonucleotides, e. g., an embodiment is an RNA that comprises terminal deoxyribonucleotides. In some embodiments, the compositions described herein comprise, 1, 2, 3, 4, 5, 6, 7, 8, 9, 10 or more polynucleotides that target one or more essential genes in one or more pest species.

In some embodiments, the compositions described herein may be incorporated in the diet of the targeted pest or may be overlaid on the top of the diet for consumption by the pest. In some embodiments, the compositions described herein are incorporated in a spray mixer and applied to the surface of a plant, such as a leaf, stem, flower or seed. In some embodiments, ingestion of the compositions described herein by a pest delivers the polynucleotide pest control agents to the gut of the pest and subsequently to the cells within the body of the pest. Ingestion of polynucleotide pest control agent by a pest permits results in down-regulation of a target gene in the pest. It is envisioned that the compositions as described herein can be incorporated into a coating or seed treatment that is applied to the seed before planting. In some embodiments, the plant or seed is a transgenic plant or seed. In some embodiments, the transgenic plant or seed expresses at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphaericus* insecticidal protein.

The plant can be any plant that is subject to infestation by an insect that can be controlled by the polynucleotides disclosed herein. Plants of particular interest include commercially important plants, including row crop plants, vegetables, and fruits, and other plants of agricultural or decorative use. Examples of suitable plants are provided under the heading "Plants". The method is especially useful for controlling an insect infestation of an ornamental plant or a crop plant. Various embodiments of the method include those wherein the plant is a plant in the family Brassicaceae, including a *Brassica* species selected from the group consisting of *B. napus, B. juncea, B. carinata, B. rapa, B. oleracea, B. rupestris, B. septiceps, B. nigra, B. narinosa, B. perviridus, B. tournefortii,* and *B. fructiculosa*. In other embodiments, the plant is selected from the group consisting of *Glycine max, Linum usitatissimum, Zea mays, Carthamus tinctorius, Helianthus annuus, Nicotiana tabacum, Arabidopsis thaliana, Betholettia excelsa, Ricinus communis, Cocus nucifera, Coriandrum sativum, Gossypium* spp., *Arachis hypogaea, Simmondsia chinensis, Solanum tuberosum, Elaeis guineensis, Olea europaea, Oryza sativa, Cucurbita maxim, Hordeum vulgare,* and *Triticum aestivum*.

The methods and compositions in the present disclosure can be used for any polynucleotides targeting any gene in a pest organism. In some embodiments, the pest is an invertebrate pest. In some embodiments, the invertebrate pest is an insect or a mite. In some embodiments, the insect is a leaf-eating insect. In some embodiments, the insect is a ground-dwelling insect. In some embodiments, the insect is a Colorado potato beetle (CPB, *Leptinotarsa decemlineata*), a bee, a Western Corn Rootworm (WCR, *Diabrotica virgifera*), a Red Flour Beetle (RFB, *Tribolium castaneum*), a European Corn Borer (ECB, *Ostrinia nubilalis*), a Black Cutworm (BCW, *Agrotis ipsilon*), a Corn Earworm (CEW, *Helicoverpa zea*), a Fall Army worm (FAW, *Spodoptera frupperda*), a Cotton Ball Weevil (BWV, *Anthonomus grandis*), a silkworm (*Bombyx mori*), *Manduca sexta, Drosophila melanogaster, Anopheles gambiae,* or *Aedes aegypti*.

The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.,* 29:189-193; Gottesman (2005) *Trends Genet.,* 21:399-404; Griffiths-Jones et al. (2005) *Nucleic Acids Res.,* 33:121-124).

Examples of invertebrate pests, especially in but not limited to southern hemisphere regions (including South and Central America) include aphids, corn rootworms, *spodoptera,* noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*), "gusano áspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (*Mocis latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterranea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various thrips species (*Frankliniella* spp.), cotton earworm (*Helicoverpa zea*), "oruga bolillera" (e. g., *Helicoverpa geletopoeon*), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion *thrips* (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*), "oruga de la alfalfa" (*Colias lesbia*), "chinche marrón" or "chinche de los cuernos" (*Dichelops furcatus*), "alquiche chico" (*Edessa miditabunda*), blister beetles (*Epicauta* spp.), "barrenador del brote" (*Epinotia aporema*), "oruga verde del yuyo colorado" (*Loxostege bifidalis*), rootknot nematodes (*Meloidogyne* spp.), "oruga cuarteadora" (*Mocis repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines*, *Meloidogyne* spp., *Belonolaimus* spp.), bananas (*Radopholus similis*, *Meloidogyne* spp., *Helicotylenchus* spp.), sugarcane (*Heterodera sacchari*, *Pratylenchus* spp., *Meloidogyne* spp.), oranges (*Tylenchulus* spp., *Radopholus* spp., *Belonolaimus* spp., *Pratylenchus* spp., *Xiphinema* spp.), coffee (*Meloidogyne* spp., *Pratylenchus* spp.), coconut palm (*Bursaphelenchus* spp.), tomatoes (*Meloidogyne* spp., *Belonolaimus* spp., *Nacobbus* spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xiphinema* spp.), cacao (*Meloidogyne* spp., *Rotylenchulus reniformis*), pineapple (*Meloidogyne* spp., *Pratylenchus* spp., *Rotylenchulus reniformis*), papaya (*Meloidogyne* spp., *Rotylenchulus reniformis*), grapefruit (*Tylenchulus* spp., *Radopholus* spp. *Belonolaimus* spp., *Pratylenchus* spp., *Xiphinema* spp., and broad beans (*Meloidogyne* spp.).

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U. S. Patent Application Publication 2006/0021087 A1, PCT Patent Application PCT/US05/11816, and in Table II of U. S. Patent Application Publication 2004/0098761 A1.

In some embodiments, the target gene encodes an essential protein of the organism. In some embodiments, the essential protein has a predicted function selected from: muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, apoptosis, and any combination thereof.

In some embodiments, the polynucleotide is a DNA, an RNA, or a DNA/RNA hybrid. In some embodiments, the polynucleotide is single-stranded or double-stranded. In some embodiments, the polynucleotide is from 10 to about 5000 nucleotides (nt) in length. In some embodiments, the polynucleotide is from 15 to about 5000 nucleotides (nt) in length. In some embodiments, the polynucleotide is from 10 to about 1500 nucleotides (nt) in length. In some embodiments, the polynucleotide is from 15 to 1500 nucleotides (nt) in length. In some embodiments, the polynucleotide is from about 20 to about 100, about 75 to about 150, about 100 to about 200, about 150 to about 300, about 200 to about 400, about 300 to about 500, about 400 to about 600, about 500 to about 700, about 600 to about 800, about 700 to 1000, about 900 to about 1200, about 1000 to about 1500, about 1200 to about 2000, about 1500 to about 2500, about 2000 to about 3000, about 2500 to about 3500, about 3000 to about 4000, about 3500 to about 4500, or about 4000 to about 5000 nt in length. In some embodiments, the polynucleotide is about 20, about 30, about 40, about 50, about 60, about 80, about 100, about 120, about 140, about 150, about 160, about 180, about 200, about 220, about 224, about 260, about 280, about 300, about 320, about 340, about 360, about 380, about 400, about 420, about 440, about 460, about 480, about 500, about 550, about 600, about 650, about 700, about 750, about 800, about 850, about 900, about 950, about 1000, about 1100, about 1200, about 1300, about 1400, about 1500, about 2000, about 2500, about 3000, about 3500, about 4000, about 4500, or about 5000 nt in length.

In one aspect, the polynucleotide comprises at least one segment of 16 or more contiguous nucleotides with a sequence of about 80%, about 81%, about 82%, about 83%, about 84%, about 85%, about 86%, about 87%, about 88%, about 89%, about 90%, about 91%, about 92%, about 93%, about 94%, or about 95% to about 100% identity with a fragment of equivalent length of a DNA of a target gene. In some embodiments, the contiguous nucleotides number at least 16, e.g., from 16 to 24, or from 16 to 25, or from 16 to 26, or from 16 to 27, or from 16 to 28. In some embodiments, the contiguous nucleotides number at least 18, e.g., from 18 to 24, or from 18 to 28, or from 20 to 30, or from 20 to 50, or from 20 to 100, or from 50 to 100, or from 50 to 500, or from 100 to 250, or from 100 to 500, or from 200 to 1000, or from 500 to 2000, or even greater. In some embodiments, the contiguous nucleotides number more than 16, e.g., 17, 18, 19, 20, 21, 22, 23, 24, 25, 26, 27, 28, 29, 30, or greater than 30, e.g., about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 350, about 400, about 450, about 500, about 600, about 700, about 800, about 900, about 1000, or greater than 1000 contiguous nucleotides. In some embodiments, the polynucleotide comprises at least one segment of at least 21 contiguous nucleotides with a sequence of 100% identity with a fragment of equivalent length of a DNA of a target gene. In some embodiments, the polynucleotide is a double-stranded nucleic acid (e.g., dsRNA) with one strand comprising at least one segment of at least 21 contiguous nucleotides with 100% identity with a fragment of equivalent length of a DNA of a target gene; expressed as base-pairs, such a double-stranded nucleic acid comprises at least one segment of at least 21 contiguous, perfectly matched base-pairs which correspond to a fragment of equivalent length of a DNA of a target gene, or the DNA complement thereof. In some embodiments, each segment contained in the polynucleotide is of a length greater than that which is typical of naturally occurring regulatory small RNAs, for example, each segment is at least about 30 contiguous nucleotides (or base-pairs) in length. In some embodiments, the total length of the polynucleotide is between about 50 to about 5000 nucleotides (for single-stranded polynucleotides) or base-pairs (for double-stranded polynucleotides). In some embodiments, the polynucleotide is a dsRNA of between about 50 to about 5000 base-pairs. In some embodiments, the polynucleotide is topically provided to the surface of a plant or *Leptinotarsa* species.

In certain embodiments, the polynucleotide is a double-stranded RNA of from 50 to 5000 base-pairs in length.

In some embodiments, the mixture of polynucleotide and cationic polymer is taken up through the digestive system of the organism, or through the respiratory system of the organism. In some embodiments, the mixture is provided for dietary intake by the organism in a form suitable for ingestion. In some embodiments, the mixture is provided as an insect bait. In certain embodiments, the polynucleotide compositions or mixture further comprise an expedient selected from corn syrup, sugar syrup, sugar solid, sugar semi-solids, pollen, soy protein, pollen, protein mixtures, and any combination thereof.

In some embodiments, the cationic polysaccharide is hydrolysable in the digestive tract of the pest. In some embodiments, the cationic polymer is hydrolysable by one or more enzymes in the digestive tract of the pest. In one embodiment, the polysaccharide is starch. In one embodiment, the polysaccharide is cornstarch. In another embodiment, the polysaccharide is guar gum. In some embodiments, the one or more enzymes are selected from: an amylase, a cellulase, a hemicellulase, a glucosidase, a galactosidase, a chitinase, an acetylglucosaminidase, a fructosidase, a trehalase, a lysozyme, a mannosidase, and any combination thereof.

In certain embodiments, the polynucleotide mixture is applied onto a leaf. In some embodiments, the leaf is from a plant selected from: alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, *eucalyptus*, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, *papaya*, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini plants.

In certain embodiments, the compositions described herein may be applied onto a surface of a leaf. In some embodiments, the polynucleotide is applied at a concentration from about 1 ng/ml to about 1000 μg/ml. In some embodiments, the polynucleotide is applied at a concentration from about 1 ng/ml to about 500 μg/ml, from about 1 ng/ml to about 250 μg/ml, from about 1 ng/ml to about 100 μg/ml, from about 1 ng/ml to about 50 μg/ml, from about 1 ng/ml to about 25 μg/ml, from about 1 ng/ml to about 10 μg/ml, from about 1 ng/ml to about 5 μg/ml, from about 1 ng/ml to about 1 μg/ml, from about 0.01 μg/ml to about 500 μg/ml, from about 0.01 μg/ml to about 250 μg/ml, from about 0.01 μg/ml to about 100 μg/ml, from about 0.01 μg/ml to about 50 μg/ml, from about 0.01 μg/ml to about 25 μg/ml, from about 0.01 μg/ml to about 10 μg/ml, from about 0.01 μg/ml to about 5 μg/ml, from about 0.01 μg/ml to about 1 μg/ml, from about 0.01 μg/ml to about 0.5 μg/ml, from about 0.01 μg/ml to about 0.1 μg/ml, from about 0.05 μg/ml to about 1000 μg/ml, from about 0.05 μg/ml to about 500 μg/ml, from about 0.05 μg/ml to about 250 μg/ml, from about 0.05 μg/ml to about 100 μg/ml, from about 0.05 μg/ml to about 50 μg/ml, from about 0.05 μg/ml to about 25 μg/ml, from about 0.05 μg/ml to about 10 μg/ml, from about 0.05 μg/ml to about 5 μg/ml, from about 0.05 μg/ml to about 1 μg/ml, from about 0.05 μg/ml to about 0.5 μg/ml, from about 0.05 μg/ml to about 0.1 μg/ml, from about 0.1 μg/ml to about 1000 μg/ml, from about 0.1 μg/ml to about 500 μg/ml, from about 0.1 μg/ml to about 250 μg/ml, from about 0.1 μg/ml to about 100 μg/ml, from about 0.1 μg/ml to about 50 μg/ml, from about 0.1 μg/ml to about 25 μg/ml, from about 0.1 μg/ml to about 10 μg/ml, from about 0.1 μg/ml to about 5 μg/ml, from about 0.1 μg/ml to about 1 μg/ml, from about 1 μg/ml to about 1000 μg/ml, from about 1 μg/ml to about 500 μg/ml, from about 1 μg/ml to about 250 μg/ml, from about 1 μg/ml to about 100 μg/ml, from about 1 μg/ml to about 50 μg/ml, from about 1 μg/ml to about 25 μg/ml, from about 1 μg/ml to about 10 μg/ml, from about 1 μg/ml to about 5 μg/ml, from about 10 μg/ml to about 1000 μg/ml, from about 10 μg/ml to about 500 μg/ml, from about 10 μg/ml to about 250 μg/ml, from about 10 μg/ml to about 100 μg/ml, from about 10 μg/ml to about 50 μg/ml, from about 10 μg/ml to about 25 μg/ml, from about 50 μg/ml to about 1000 μg/ml, from about 50 μg/ml to about 500 μg/ml, from about 50 μg/ml to about 250 μg/ml, from about 50 μg/ml to about 100 μg/ml, from about 100 μg/ml to about 1000 μg/ml, from about 100 μg/ml to about 500 μg/ml, or from about 100 μg/ml to about 250 μg/ml.

In some embodiments, the polynucleotide is applied at a concentration of about 1 ng/ml, about 5 ng/ml. about 10 ng/ml, about 15 ng/ml, about 20 ng/ml, about 25 ng/ml, about 30 ng/ml, about 40 ng/ml, about 50 ng/ml, about 60 ng/ml, about 70 ng/ml, about 80 ng/ml, about 90 ng/ml, about 0.1 μg/ml, about 0.2 μg/ml, about 0.5 μg/ml, about 1 μg/ml, about 5 μg/ml, about 10 μg/ml, about 20 μg/ml, about 30 μg/ml, about 40 μg/ml, about 50 μg/ml, about 60 μg/ml, about 70 μg/ml, about 80 μg/ml, about 90 μg/ml, about 100 μg/ml, about 200 μg/ml, about 300 μg/ml, about 400 μg/ml, about 500 μg/ml, about 600 μg/ml, about 700 μg/ml, about 800 μg/ml, about 900 μg/ml, or about 1000 μg/ml.

In some embodiments, the compositions described herein may be re-applied at least once, at least twice, or at least three times onto the surface of the leaf at an interval of at least 24 hours after the initial application. In some embodiments, the interval of the reapplied mixture is from about 24 hours to about 14 days. In some embodiments, the interval of the reapplied mixture is about 24 hours, about 36 hours, about 48 hours, or about 72 hours. In other embodiments, the interval of the reapplied mixture is from about 1 day to about 14 days, from about 2 days to about 10 days, or from about 2 days to about 5 days. In yet other embodiments, the interval of the reapplied mixture is about 3 days, about 4 days, about 5 days, about 6 days, about 7 days, about 8 days, about 9 days, about 10 days, about 11 days, about 12 days, about 13 days, or about 14 days.

In some embodiments, at least 10%, at least 20%, at least 30%, at least 40%, at least 50%, at least 60%, at least 70%, at least 80%, or at least 90% of the total area on the surface of the leaf is in contact with a composition as described herein.

In some embodiments, the compositions described herein may be provided in a form selected from the group consisting of a solid, liquid, powder, suspension, emulsion, spray, encapsulation, microbeads, carrier particulates, film, matrix, soil drench, insect diet or insect bait, and seed treatment. In some embodiments, a pesticidal composition is provided in a form that is ingested by the insect, such as in a liquid, emulsion, or powder applied to a plant on which the insect feeds, or in the form of bait. The pesticidal compositions can further include one or more components selected from the group consisting of a carrier agent, a surfactant, an organosilicone, a polynucleotide herbicidal molecule, a non-polynucleotide herbicidal molecule, a non-polynucleotide pesticide, a safener, an insect attractant, and an insect growth regulator. The pesticidal compositions can further include at least one pesticidal agent selected from the group consisting of a patatin, a plant lectin, a phytoecdysteroid, a *Bacillus thuringiensis* insecticidal protein, a *Xenorhabdus* insecticidal protein, a *Photorhabdus* insecticidal protein, a *Bacillus* laterosporous insecticidal protein, and a *Bacillus sphaericus* insecticidal protein. In some embodiments, the combination of the recombinant RNA molecule and the pesticidal agent provides a level of insect control that is synergistic, i. e., greater than the sum of the effects of the recombinant RNA molecule and the pesticidal agent components if tested separately.

The following Examples are presented for the purposes of illustration and should not be construed as limitations.

Example 1

This example describes preparation of a cross-linked cationic polysaccharide. More specifically this example illustrates cationic functionalization of a starch with glycidyl trimethylammonium chloride (GTAC). The procedure described is suitable for cationic functionalization of various starches (e. g., corn starch, potato starch, rice starch, tapioca starch, and wheat starch) as well as of maltodextrins.

In these examples, the polysaccharide particles are identified by the ratio of GTAC and $POCl_3$ (or another cross-linker) to starch (or other polysaccharide) used in their production as well as by the polysaccharide type. For example, C56_3 indicates that the particle was derived from corn starch ("C") which was reacted with 56 grams of GTAC (>90%) per 100 grams of corn starch and 3 grams of $POCl_3$ per 100 grams of corn starch.

In a 500-milliliter round-bottom flask equipped with a stir bar, 8 grams of corn starch (unmodified waxy corn starch of essentially pure amylopectin) was dissolved in 10 grams of 2.5 N NaOH plus 190 milliliters of water. Glycidyl trimethylammonium chloride (GTAC) (>90%) was added at different GTAC-to-starch ratios and the mixture was stirred, uncapped in a 60 degrees Celsius oil bath. Results are provided in Table 1. After the reaction, most of the solutions were clear except for C20, which was somewhat opalescent.

TABLE 1

| Batch | GTAC:starch | GTAC used | Reaction time | Mass recovered |
|---|---|---|---|---|
| C40 | 0.4 g/g | 3.2 g | 6 h | 203 g |
| C20 | 0.2 g/g | 1.6 g | 16 h | 187 g |
| C10 | 0.1 g/g | 0.8 g | 4 h | 208 g |
| C05 | 0.05 g/g | 0.4 g | 4 h | 209 g |
| C02 | 0.02 g/g | 0.16 g | 15 h | 192 g |

The same protocol was used to prepare cationic maltodextrins, using 8 grams of the maltodextrin in place of corn starch and performing the reaction under a static nitrogen atmosphere (except for MD5_5). Two maltodextrins were used. One, "MD5" (Aldrich catalogue number 419672, CAS number 9050-36-6, Sigma-Aldrich, 3050 Spruce St., St. Louis, Mo. 63103) with higher molecular weight, has a labelled dextrose equivalent (DE) of 4.0-7.0. The other maltodextrin, "MD17" (Aldrich catalogue number 419699, CAS number 9050-36-6, Sigma-Aldrich, 3050 Spruce St., St. Louis, Mo. 63103), has a labelled DE of 16.5-18.5. Results are provided in Table 2. The reaction mixtures using maltodextrins were darker than those using corn starch, presumably due to reactions of the aldehydes. Viscosity was water-like.

TABLE 2

| Batch | GTAC:maltodextrin | GTAC used | Reaction time | Mass recovered |
|---|---|---|---|---|
| MD5_20 | 0.2 g/g | 1.6 g | 12 h | 204 g |
| MD5_05 | 0.05 g/g | 0.4 g | 5 h | 201 g |
| MD5_02 | 0.02 g/g | 0.16 g | 5 h | 207 g |
| MD17_20 | 0.2 g/g | 1.6 g | 15 h | 204 g |
| MD17_05 | 0.05 g/g | 0.4 g | 5 h | 204 g |
| MD17_02 | 0.02 g/g | 0.16 g | 5 h | 212 g |

Example 2

This Example describes the preparation of two starches, C20 and C56. In a 1-liter round-bottom flask equipped with a stir bar, 20 grams of corn starch (unmodified waxy corn starch of essentially pure amylopectin) was dissolved in 25 grams of 2.5 N NaOH plus 450 milliliters of water. Glycidyl trimethylammonium chloride (GTAC) (>90%) was added and the mixture was stirred overnight, uncapped, in a 60 degrees Celsius oil bath. The product was a light-colored homogeneous solution.

TABLE 3

| Batch | GTAC:Starch | GTAC used | Reaction time | Mass Recovered |
|---|---|---|---|---|
| C20 | 20% | 4.0 g | 23 h | 463.3 g |
| C56 | 56% | 11.2 g | 19 h | 476.1 g |

Example 3

This Example describes the cross-linking of cationic starches such as those provided by procedures described in Examples 1 and 2. Phosphoryl chloride ($POCl_3$) was used as the cross-linking agent in a reversed-phase emulsion. Limonene, which has low toxicity, was used as the hydrophobic solvent.

260 grams of a 1.0% solution of Tween 80 in limonene was transferred to a 16-ounce wide-mouthed jar equipped with a thermocouple. The jar was wrapped with heating tape and the temperature controller set to 75 degrees Celsius with agitation using a Turrax high shear mixer during heat-up and the reaction. About 50 grams of the cationic starch solution from Examples 1 or 2 or similar preparation, equivalent to 2.0 grams starch, was added during the beginning of the heat-up. A 10% solution of $POCl_3$ in limonene was added when the temperature reached 71 degrees Celsius, and the mixture was agitated at 10,000 rpm for 30 minutes while maintaining a temperature of 75±1 degrees Celsius. Emulsification was excellent. The mixture was then immediately poured into a separatory funnel. After 2 minutes, a cloudy aqueous layer was collected from the bottom and 150 milliliters of absolute ethanol was added to precipitate the cross-linked cationic starch.

After ethanol addition, the cross-linked cationic starch rapidly settled to the bottom of the container. After allowing about three minutes to complete precipitation and settling, the product was isolated by decanting the supernatant. Typically, several batches prepared in this way were combined before recovering the cross-linked cationic starch product. The product was then dried overnight at 55 degrees Celsius under 24" Hg vacuum with nitrogen purge. Recoveries are shown in Table 4.

TABLE 4

| Starch type | Batch | Starch | POCl$_3$:starch | POCl$_3$ | Yield |
|---|---|---|---|---|---|
| C56_3 | 1 | C56, 47.6 g | 3% | 6 g | 1.6 g |
| C56_3 | 2 | C56, 47.6 g | 3% | 6 g | 1.0 g |
| C56_3 | 3, 4 | C56, 47.6 g | 3% | 6 g | 2.6 g |
| C56-3 | 5-9 | C56, 47.6 g | 3% | 6 g | 8.0 g |
| C20_1 | 1-5 | C20, 46.3 g | 1% | 2 g | 7.7 g |
| C20_1 | 6-7 | C20, 46.3 g | 1% | 2 g | 4.1 g |

Example 4

This example further illustrates cross-linking of cationic starch particles. This example describes a reaction that is carried out on a smaller scale than that described in Example 3 and that uses filtration to recover the product. This procedure is suitable for cationic starches which are less hydrophilic. The resulting cross-linked cationic starches were tested for solubility in boiling water. Particles which dissolved in boiling water were selected for combining with polynucleotides (e. g., dsRNA) because they are more resistant to settling and agglomeration.

65 grams of a 1.0% solution of Tween 80 in limonene was transferred to a 4-ounce jar. The jar was wrapped with heating tape and the temperature controller set to 75 degrees Celsius with agitation using the Turrax during heat-up and the reaction. About 12 grams of cationic starch solution from Example 1, equivalent to 0.5 grams starch, was added during the beginning of the heat-up. The 0.5% solution of POCl$_3$ in limonene was added when the temperature reached 71 degrees Celsius, and the mixture was agitated at 10,000 rpm for 30 minutes while maintaining a temperature of 75±1 degrees Celsius. Emulsification was excellent. The mixture was then immediately poured into a separatory funnel which had been heated in an oven. After 1 minute, a cloudy aqueous layer was collected from the bottom in a 50-milliliter centrifuge tube. 35 milliliters of absolute ethanol was added. The solution remained cloudy. The solution was filtered immediately with a coarse Buchner funnel, recovering the precipitate as a white powder; the pale yellow filtrate was discarded. The precipitate was rinsed with ethanol and dried for overnight at 50 degrees Celsius under 24" Hg vacuum with nitrogen purge. Recoveries are shown in Table 5.

TABLE 5

| Batch | Starch | POCl$_3$:starch | POCl$_3$ sol. | Yield | Dissolves in boiling H$_2$O? | After cooling |
|---|---|---|---|---|---|---|
| C40_5 | C40, 12.7 g | 5% | 5 g | 0.22 g | No | — |
| C40_2 | C40, 12.7 | 2% | 2 g | — | Yes | Clear |
| C20_5 | C20, 11.7 g | 5% | 5 g | 0.25 g | No | — |
| C20_2 | C20, 11.7 g | 2% | 2 g | 0.28 g | Yes | Slightly cloudy |
| C20_1 | C20, 11.7 g | 1% | 1 g | 0.32 g | Yes | Clear |
| C10_5 | C10, 13.0 g | 5% | 5 g | 0.28 g | No | — |
| C02_2 | C02, 12.0 g | 2% | 2 g | 0.27 | Yes | Slightly cloudy |

Cationic maltodextrins were subjected to the same procedure, but recovery of cross-linked product was low.

Example 5

This example describes digestion of cross-linked cationic starches into free glucose by the common digestive enzyme amyloglycosidase. Such enzymatic cleavage of the cationic starches in a pest organism's digestive tract is expected to free the associated polynucleotide from the cationic cross-linked starch matrix.

500 microliters of starches C56_3 and C05_5 prepared by the methods of Examples 3 and 4, respectively, were dissolved in water by boiling for 10 minutes; undissolved material was removed by centrifugation. The starch solutions were incubated with 50 microliters of 0.01 U/microliter amylase glycosidase at 55 degrees Celsius for four hours along with samples without enzyme as controls. After four hours, the enzymatic reaction was terminated by heating to 100 degrees Celsius for 10 minutes followed by centrifugation.

Free glucose was first converted to glucose-6-phosphate (G-6-P) in the presence of adenine triphosphate (ATP) catalyzed by hexose kinase (HK). The resulting G-6-P was oxidized to gluconate-6-phosphate (gluconate-6-P) catalyzed by glucose-6-phosphate dehydrogenase (G-6-PDH) in the presence of nicotinamide adenine dinucleotide phosphate (NADP), which was converted to its reduced form, NADPH. The formation of NADPH was monitored with a UV spectrophotometer at 340 nanometers.

10 microliters of the digested cationic starch solution was combined with 200 microliters of ultrapure water and 100 microliters of NADP+G-6-PDH assay buffer and mixed well. A background measurement at 340 nanometers was obtained. 10 microliters of HK/ATP buffer was added and a second measurement at 340 nanometers was obtained after five minutes.

Free glucose was calculated by measuring the increase in NADPH absorbance at 340 nanometers. The free glucose produced is calculated as a weight percent relative to the original cross-linked cationic starch. The starch with a higher level of cationic functionalization (C56_3) produced less free glucose than C05_5. However, both starches were readily cleaved enzymatically.

The composition of the buffers used in this protocol were as follows.

Amylase glycosidase: AG 0.01 U/microliter in 100 mM sodium acetate pH 4.65.

G-6-PDH/NADP buffer: 100 mM Triethanolamine pH 8+10 mM MgCl$_2$+0.8 mM NADP+G-6-PDH 0.0061 microgram/microliter.

HK/ATP buffer: 500 mM Triethanolamine, pH8+HK 0.04 U/microliter+ATP 0.02 micromoles/microliter.

Example 6

This example describes a method to quantify the degree of cationic substitution in the cationic cross-linked corn starches. Elemental analysis of several starches prepared by the procedure of Examples 1 and 2 was conducted for carbon, hydrogen, nitrogen, and phosphorus. Nitrogen was quantified only (>0.5%) for GTAC:starch ratios. The analysis allows the degree of GTAC cationic substitution to be determined, which is reported on the table below as the ratio of cationic GTAC groups to glucose rings in the starch. The degree of cross-linking is qualitatively indicated by the phosphorus content; phosphorus levels generally increase with increasing amounts of POCl3 used in the preparation of the particles.

TABLE 6

| Starch | % C | % H | % N | % P | % glucose with cationic substitution |
|---|---|---|---|---|---|
| C02_2 | 37.1% | 6.74% | <0.5% | 0.335% | — |
| C02_5 | 37.74% | 6.83% | <0.5% | 0.746% | — |
| C05_5 | 39.83% | 7.03 | <0.5% | 0.278% | — |
| C20_1 | 40.42% | 7.18% | 0.53% | 0.107% | 7.2% |
| C40_5 | 38.25% | 7.11% | 0.83% | 0.530% | 12.6% |
| C56_3 | 39.50% | 7.19% | 0.95% | 0.179% | 14.1% |

Example 7

This example illustrates a rainfastness assay, useful in comparing stability of polynucleotides, such as double-stranded RNAs, applied to plants. More specifically, this example demonstrates that complexing double-stranded RNA with cross-linked cationic corn starch protects the RNA from being washed off by rain.

Plants varieties used for this assay were either Big Cherry tomato or Atlantic potato. Plants were propagated and assays were conducted in growth chambers using a 16 hour light:8 hour dark cycle. Temperatures during the light cycle ranged from 23-27 degrees Celsius and during the dark cycle from 20-22 degrees Celsius. Relative humidity was maintained at 50-75%.

On the day of foliar application, a double-stranded RNA (dsRNA) designed to suppress a target gene of Colorado potato beetle (*Leptinotarsa decemlineata*) was diluted into test formulations to a final concentration of 1 microgram/milliliter. The formulations were applied to plants at a rate of 30 gallons per acre using a SS9501E nozzle. After treatment, plants were returned to the growth chamber for approximately 18-24 hours. They were then placed in a rain simulator and exposed to the equivalent of 0.25 inches of rain over a 25 minute period. Plants not exposed to simulated rainfall served as controls.

After the plants dried, tissue samples were collected and transferred to 96-well plates. Total plant RNA was extracted from tissue using a 96-well plant RNA extraction kit (Omega Bio-Tek) and the total RNA levels were determined via NanoDrop. *Leptinotarsa*-specific dsRNA levels per microgram total RNA were determined using Affymetrix's technology through the use of labelled nucleic acid probes that specifically hybridize to the dsRNA of interest.

Various formulations (Table 7) were evaluated for their rainfastness on leaves. *Leptinotarsa*-specific RNA levels, relative to total RNA, were determined with and without the simulated rain event and reported as nanogram dsRNA per microgram of total RNA. In addition to cationic cross-linked corn starch C56_3, paraffin or candelilla wax, commercial stickers (Tactic, from Loveland) and a penetrant (Liberate from Loveland) were evaluated. The wax emulsions were formulated as disclosed in Table 8.

TABLE 7

| Formulation | dsRNA pre-rain | dsRNA post-rain |
|---|---|---|
| 1% Tween 85 only | 24.8 | 2.1 |
| 0.19% Tactic + 0.25% Liberate | 16.3 | 4.1 |
| Tween 85/paraffin wax | 26.8 | 0.4 |
| Brij 10/candelilla wax | 23.2 | 0.4 |
| Silwet L77/candelilla wax | 22.7 | 1.9 |
| 1% C56_3 + 0.2% Proxel GXL + 1% Benzophenone-9 + 0.02% Silwet L77 | 6.3 | 7.4 |

TABLE 8

| Compound | Function | Amount (percent) |
|---|---|---|
| Candelilla or paraffin wax | Wax | 0.5 |
| PEG | Wetting agent | 3 |
| Tween 85/Brij 10 or Silwet L-77 | Dispersant | 1%, 1%, 0.1% |
| Soy Oil | Cosolvent | 3 |
| Benzophenone-9 | Photo protectant | 1 |
| Kelzan CC | Thickener | 0.12 |
| Proxel | Biocide | 0.24 |
| Water | Carrier | To 100% |

In this experiment, the *Leptinotarsa*-specific dsRNA levels on plants treated with cationic cross-linked corn starch (C56_3) did not decrease after a simulated rain event, although the dsRNA levels were low possibly due to C56_3 interfering with the assay. Plants treated with *Leptinotarsa*-specific dsRNA, with or without stickers and penetrants, generally suffered about 90% loss of dsRNA.

Example 8

This example illustrates a defoliation assay, useful in comparing efficacy of compositions containing a cross-linked cationic polysaccharide and a polynucleotide, applied to plants. More specifically, this example demonstrates that complexing double-stranded RNA with cross-linked cationic corn starch protects the dsRNA from being washed off by rain and provides improved protection from defoliation by an herbivorous insect pest.

Formulations containing a ~280 base-pair double-stranded RNA (dsRNA) designed to suppress a target gene of Colorado potato beetle (*Leptinotarsa decemlineata*) were applied to tomato or potato plants by the same procedure as Example 7; after simulated rainfall, efficacy was evaluated with either plant defoliation or insect viability readout. As in Example 7, this assay used 1 microgram/milliliter of the dsRNA in all formulations except for the control formulation which contained only 1% Tween 85, a mild anionic surfactant. One formulation contained Tactic, a commercial polymeric "sticker" from Loveland. These were compared to a formulation containing 10 microgram/milliliter of cationic starch C56_3.

Each treated plant was individually caged using mesh sleeves, infested with neonatal Colorado potato beetle larvae, and returned to the growth chamber for 12-14 days. At the end of this period, plants were uncaged and percent defoliation (relative to uninfested, caged controls) and percent recovery of viable insects determined.

Table 9 shows percent defoliation of plants with and without the simulated 0.25-inch rainfall event. Lower levels of defoliation are the measure of efficacy. In the absence of dsRNA (i. e., the Tween 85 control), 46% defoliation was observed. All formulations with dsRNA suppressed defoliation to 15-20%, but only the formulation containing the cross-linked cationic starch composition retained activity after rainfall, effectively limiting defoliation to 23%. Table 9 also shows percent recovery of viable insects; these data also indicated greater efficacy of the formulation containing the cross-linked cationic starch composition.

TABLE 9

| | Percent Defoliation | | Percent recovery of viable insects | |
|---|---|---|---|---|
| Formulation | Pre-rain | Post-rain | Pre-rain | Post-rain |
| 1% Tween 85 | 46% | — | 81% | — |
| dsRNA + 1% Tween 85 | 14% | 50% | 22% | 67% |

TABLE 9-continued

| Formulation | Percent Defoliation | | Percent recovery of viable insects | |
|---|---|---|---|---|
| | Pre-rain | Post-rain | Pre-rain | Post-rain |
| dsRNA + Tactic | 17% | 44% | 16% | 54% |
| 10:1 C56_3 cationic starch + dsRNA | 18% | 23% | 21% | 32% |

Example 9

This example describes a feeding assay useful in comparing efficacy of compositions containing a cross-linked cationic polysaccharide and a polynucleotide. More specifically, this example demonstrates that dsRNA that cause mortality in Colorado potato beetle continue to cause mortality after the dsRNA is complexed with cationic cross-linked corn starch.

Formulations containing a ~280 base-pair double-stranded RNA (dsRNA) designed to suppress a target gene of Colorado potato beetle (*Leptinotarsa decemlineata*) were prepared. Formulations containing the dsRNA at final concentrations of 100, 50, 25, or 0 nanogram/milliliter, combined with low-molecular weight polyethyleneimine (800 daltons, "PEI 800"), high molecular weight polyethylene (750,000 Dalton, "PEI 750 k), chitosan, gelatin, xanthan gum, and cationic starch C56_3 were formulated as follows:

PEI 800 (2 milligram/milliliter)+25 mM sodium acetate (pH 5.2)

PEI 750 k (2 milligram/milliliter)+25 mM sodium acetate (pH 5.2)

Gelatin (1%)+25 mM sodium acetate (pH 5.2)

Chitosan+25 mM sodium acetate (pH 5.2)

Xanthan gum (0.05%)

Cationic starch, C56_3 (1%)+1% Benzophenone 9+0.02% Proxel GXL (antimicrobial).

An artificial diet for Colorado potato beetle was prepared and dispensed into multi-well plates. Immediately prior to overlay of the dsRNA formulations, diet-containing multi-well plates were partially dehydrated to facilitate absorption of the formulated dsRNAs into the diet. The dsRNA formulations were then aliquoted onto the diet, and after the formulations were absorbed, each well was infested with a single neonatal CPB larvae. Plates were sealed with covers contained small holes allowing gas exchange, and were incubated for 10-12 days at 27 degrees Celsius, 50% RH, using a 16-h light:8-h dark cycle. At the end of the incubation period, the plates were scored for insect mortality. Percent mortality data are shown in Table 10.

TABLE 10

| Formulation | Diet Concentration nanogram/milliliter | | | | |
|---|---|---|---|---|---|
| | 0 | 10 | 25 | 50 | 100 |
| Untreated control | 13.7% | | | | |
| PEI 800 | | 8.3% | 41.7% | 79.2% | 83.3% |
| PEI 750k | | 7.2% | 0% | 26.2% | 0% |
| Gelatin | | 45.8% | 45.8% | 70.8% | 84.7% |
| Chitosan | | 0% | 25.0% | 33.3% | 95.8% |
| Xanthan Gum | | 87.5% | 70.2% | 75.0% | 91.7% |
| Cationic Starch | | 58.3% | 100% | 87.5% | 91.7% |

These data demonstrates that dsRNA retains its efficacy when conjugated to cross-linked cationic corn starch. Other stickers such as gelatin also do not interfere with activity, but they have not been shown to provide foliar stability.

Example 10

This example describes an assay useful in comparing photostability under field conditions of compositions containing a cross-linked cationic polysaccharide and a polynucleotide. More specifically, this example demonstrates that formulations containing a dsRNA complexed with cationic cross-linked corn starch and also containing an anionic photostabilizer (Benzophenone 9) exhibited improved photostability when applied to plants in the field.

Formulations containing a ~280 base-pair double-stranded RNA (dsRNA) designed to suppress a target gene of Colorado potato beetle (*Leptinotarsa decemlineata*) were prepared. Formulations containing the dsRNA, combined with 1% cationic cross-linked corn starches C56_3 and C05_5 along with 1% Benzophenone 9, or combined with commercial "stickers" (Amaze Gold, Attach, Bond, Liberate, and Tactic) from Loveland used at the labelled rate. As a control, the dsRNA was also applied as a solution with Tween 85 surfactant but without stickers or cationic starches; some of the control plants were protected with a shade cloth. No rain occurred over the three days of the test, thus any loss of dsRNA was likely to be primarily due to photolysis. The observed protective effective of the shade cloth supports this.

Tomato plants were seeded in growth chambers, and were transplanted to the field at least one week prior to treatment. Formulations containing dsRNA were prepared immediately prior to treatment and were applied at 5 g/acre at a rate of 30 gallons per acre using a pressurized sprayer. Tissue samples were collected at t=0, 1, 2, and 3 days post-treatment, and dsRNA levels were determined using Quantigene assays. The dsRNA amounts measured on tomato plants (given as nanograms of dsRNA per microgram of total RNA in the leaf disk samples) is shown in Table 11.

TABLE 11

| Formulation | Day 0 | Day 1 | Day 2 | Day 3 |
|---|---|---|---|---|
| dsRNA/Tween 85 in sunlight | 474 | 15 | 3 | 1 |
| dsRNA/Tween 85 under shade cloth | 371 | 41 | 40 | 33 |
| Amaze Gold | 219 | 3 | 0 | 0 |
| Attach | 243 | 7 | 5 | 2 |
| Bond | 214 | 11 | 5 | 2 |
| Tactic | 211 | 10 | 7 | 3 |
| C56_3 | 313 | 30 | 29 | 11 |
| C05_5 | 270 | 31 | 73 | 102 |

Example 11

This example describes an electrophoretic mobility shift assay (EMSA) useful in comparing binding efficiency of a polynucleotide to different polysaccharides at different weight/weight (w/w) ratios. More specifically, this example compares the binding efficiency of a dsRNA to several cross-linked cationic corn starches at different weight/weight (w/w) ratios of dsRNA to corn starch in the prepared formulations.

A stock solution of 1 milligram/milliliter of cross-linked cationic corn starch in water was prepared by weighing out the starch and dissolving in water either at room temperature or with boiling the resulting solution at 100 degrees Celsius for 15 minutes. If heated to 100 degrees Celsius, the solution was allowed to cool to room temperature before formulation with the polynucleotide. The polynucleotide used in all binding assays was a ~400 base-pair double-stranded RNA (dsRNA) designed to suppress a target gene of Colorado potato beetle (*Leptinotarsa decemlineata*). The cross-linked cationic corn starches tested were C20_5, C40_2, or C20_1 (Table 12). The formulations were prepared by mixing the dsRNA (100 microgram/milliliter) with the C20_5, C40_2, or C20_1 cross-linked cationic starch solutions at a 1:5 w/w ratio.

TABLE 12

| Sample | Starch type | GTAC:Starch | $POCl_3$: starch | Dissolves in boiling $H_2O$? | Dissolves in room temperature $H_2O$? |
|---|---|---|---|---|---|
| C40_5 | Corn starch | 0.4 g/g | 5% | No | No |
| C20_5 | Corn starch | 0.2 g/g | 5% | No | No |
| C10_5 | Corn starch | 0.1 g/g | 5% | No | No |
| C40_2 | Corn starch | 0.4 g/g | 2% | Yes | No |
| C20_2 | Corn starch | 0.2 g/g | 2% | Yes | No |
| C20_1 | Corn starch | 0.2 g/g | 1% | Yes | No |

Various dsRNA:starch ratios were tested with other cationic starches. For starches C56_3, C05_5, C02_2, C40_5, and hydroxypropyl cellulose (HPC) the dsRNA:starch ratios were 1:1, 1:2, 1:5 and 1:10 w/w, respectively. Binding of dsRNA to the starches was evaluated by EMSA on pre-cast 3% agarose containing gels stained with ethidium bromide. Twenty microliters of starch formulation were mixed with 5 microliters of nucleic acid loading buffer; twenty microliters of the resulting solution were loaded on the gel in 1×TBE buffer. The gel was run for 1 h at 100 V and visualized by Image Lab software. A dose-dependent decrease in electrophoretic mobility was observed for dsRNA bound to cationic starches C56_3 and C40_5, indicating tighter binding of dsRNA to the cross-linked cationic starch particle. It is possible that more cationic charge content and less cross-linking conformationally favors binding of the cationic starch to the dsRNA.

Example 12

This example describes compositions including a polynucleotide and a cross-linked cationic starch, and methods and formulations using these compositions for controlling insect pests. More specifically, this example describes control of insect pests infesting potato plants by foliar spray application of formulations containing double-stranded RNA with cross-linked cationic corn starch.

Field trials to test efficacy of formulations containing double-stranded RNA with cross-linked cationic corn starch were carried out in potato fields in multiple locations. The polynucleotide used was a ~400 base-pair double-stranded RNA (dsRNA) designed to suppress a target gene of Colorado potato beetle (*Leptinotarsa decemlineata*). The formulations were applied as foliar sprays. The primary insect pest was Colorado potato beetle (CPB, *Leptinotarsa decemlineata*). Secondary insect species that could be present included potato leafhopper (*Empoasca fabae*), potato aphid (*Macrosiphum euphorbiae*), and green peach aphid (*Myzus persicae*).

The field protocol design and methods used were as follows:

Variety: Variety managed by local sites.

Plot Size: Two row plots—25 ft planted and 12 ft alley with row spacing of 30 inches and within row spacing of 12 inches. Plants in center rows were used for other in-season data collection. Alleyways between plots were left fallow.

Border Rows: Border rows can be two outside non-planting rows or 15 feet of bare ground.

Locations: Fields with history of presence of Colorado potato beetle were prioritized. Best planting practices for the area were followed.

Design: RCB, 4 replications

Treatment Application: Treatments and commercial standards provided by Monsanto. At least two successive applications, spaced one week apart, will be applied to the potato foliage.

First Treatment Timing: 10-20% hatch of CPB larvae

Application facilities: $CO_2$ backpack sprayer, 4 nozzle boom, 20 inch spacing, 30 GPA, 40 psi.

Inoculation method: Natural Infestation

Pests: Primarily Colorado potato beetle

Data Requirements:—Beetle Counts (see detail below)
Feeding Damage Assessments
Abiotic Data
Photographs and Notes
Yield Data Collection: Beetle counts due—1, 3, 7, days after initial application; 7, 14, 21 days after 2nd application. Feeding damage assessments performed when appropriate. Abiotic data, photographs and notes, yield data due 2 weeks after harvest.

Agronomic data and pest assessment methods were performed as follows:

In situ Counts:

Ten plants were randomly selected from the center two rows in each plot. The number of required insects was recorded. Sampling times included: pre-application count, 3 days after initial application count, 7 days after first application count (immediately preceding the re-application), and then again at 7, 14, and 21 days following the second application.

Data Requirements:

The following parameters were recorded:

Small larval counts (L1-L2 stages)

Large larval counts (L3-L4 stages)

CPB adults

Aphid adults and nymphs

Feeding Damage Assessments:

Feeding damage was assessed weekly after first foliar application. The percentage of the defoliation within each plot was determined using 0 to 100% scale.

Abiotic Data:

Weather data were recorded at planting and at the time of treatment application. If on farm recording was not available in-season, closest weather source was used. Temperature data included daily max temperature, minimum temperature, mean temperature. Humidity data included precipitation, humidity, % cloud cover, dew presence.

Photographs:

Each plot of a selected replication at each rating time was photographed.

Yield:

Record number of pounds tubers harvested from center two rows of plot. Report as cwt/acre (hundredweight per acre; 1 cwt/acre=0.112 metric tons/hectare).

No additional foliar or soil insecticides were applied in the research plots. Standard management practices for high yield production in local geography were employed. Weed and fungal control in all plots were maintained to minimize effects on yield. Standard pre-emergence and appropriate post-emergent herbicides and fungal/oomycete control products were used and recorded as necessary; use and record application rates were based on label recommendations for local soil and geography.

Formulations used are listed in Table 13. The formulations that included the dsRNA: C56_3 complex also included two excipients, 0.5% v/v alkyl polyglycoside surfactant and 0.1% v/v Agnique DFM 111S (defoamer). As a control, a non-polynucleotide insecticide was used.

TABLE 13

| Treatment | Formulation | Spray Rate | Stock dsRNA concentration (mg/mL) | Tank mix dsRNA concentration (mg/mL) |
|---|---|---|---|---|
| 1 | Untreated; no dsRNA | — | NA | NA |
| 2 | dsRNA 1 mg/mL + starch (C56_3) 1% w/v + 0.1% proxel + 0.1% w/v Benzophenone-9 | 0.2 g/acre | 1 | 0.0018 |
| 3 | dsRNA 1 mg/mL + starch (C56_3) 1% w/v + 0.1% proxel + 0.1% w/v Benzophenone-9 | 1 g/acre | 1 | 0.0088 |
| 4 | dsRNA 1 mg/mL + starch (C56_3) 1% w/v + 0.1% proxel + 0.1% w/v Benzophenone-9 | 5 g/acre | 1 | 0.0440 |
| 5 | Chlorantraniliprole; no dsRNA | 5 fluid oz/acre | NA | NA |

Results from the two studies are shown in the following tables. Results from a test site in Idaho are listed in Table 14 (potato yields), Table 15 (large larvae counts, measured 14 days after a single spray application), and Table 16 (area under disease progressive curve, AUDPC). Results from a test site in Wisconsin are listed in Table 17 (potato yields), Table 18 (large larvae counts, measured 14 days after the second of two spray applications), and Table 19 (area under disease progressive curve, AUDPC). Letter groups are used to show statistically significant differences; groups identified by a shared letter do not have a statistically significant difference.

TABLE 14

| Treatment | Letter group | cwt/acre | Alpha (probability) |
|---|---|---|---|
| 1 | B | 258.218 | 0.1 |
| 2 | BA | 308.853 | 0.1 |
| 3 | BA | 300.223 | 0.1 |
| 4 | A | 317.578 | 0.1 |
| 5 | A | 326.178 | 0.1 |

TABLE 15

| Treatment | Large larval counts, least-squares mean | Letter group | Alpha (probability) |
|---|---|---|---|
| 1 | 140.2 | A | 0.05 |
| 2 | 57.2 | B | 0.05 |
| 3 | 45.1 | C | 0.05 |
| 4 | 42.9 | C | 0.05 |
| 5 | 0.2 | D | 0.05 |

TABLE 16

| Treatment | AUDPC least-squares mean | Letter group | Alpha (probability |
|---|---|---|---|
| 1 | 1621.625 | A | 0.1 |
| 2 | 901.375 | B | 0.1 |
| 3 | 514.375 | C | 0.1 |
| 4 | 442 | C | 0.1 |
| 5 | 13.875 | D | 0.1 |

TABLE 17

| Treatment | Letter group | cwt/acre | Alpha (probability) |
|---|---|---|---|
| 1 | D | 153.618 | 0.1 |
| 2 | C | 213.038 | 0.1 |
| 3 | BC | 236.315 | 0.1 |
| 4 | B | 265.5 | 0.1 |
| 5 | A | 305.003 | 0.1 |

TABLE 18

| Treatment | Large larval counts, least-squares mean | Letter group | Alpha (probability) |
|---|---|---|---|
| 1 | 62.9 | A | 0.05 |
| 2 | 11 | C | 0.05 |
| 3 | 34.9 | B | 0.05 |
| 4 | 6.8 | C | 0.05 |
| 5 | 1.3 | D | 0.05 |

TABLE 19

| Treatment | AUDPC least-squares mean | Letter group | Alpha (probability) |
|---|---|---|---|
| 1 | 1406.5 | A | 0.1 |
| 2 | 699.5 | BC | 0.1 |
| 3 | 1081.125 | AB | 0.1 |
| 4 | 448.25 | BC | 0.1 |
| 5 | 146.75 | C | 0.1 |

Example 13

This example describes a method for providing a cationic guar gum by acid hydrolysis of guar gum followed by cationic functionalization with glycidyltrimethylammonium chloride (GTAC). Other suitable cationic functionalization agents which are useful in analogous reactions include, but are not limited to, 2,3-epoxypropyl-N,N,N-trimethylammonium chloride, 3-chloro-2-hydroxypropyl-N,N,N-trimethylammonium chloride, 3-chloro-2-hydroxypropyl-N,N-dimethylethanolammonium chloride, 2,3-epoxypropyl-N,N,N-trimethylammonium chloride, and 1,3-bis-(3-chloro-2-hydroxypropyl-N,N-dimethylammonium)-N-propane dichloride.

In the hydrolysis reaction, 50 grams of guar gum (max 15% moisture), was suspended in a mixture of 130 milliliters of methanol and 20 grams of concentrated HCl in a 250 milliliter round-bottom flask equipped with a stir bar. The mixture was stirred, uncapped, in a 60 degrees Celsius oil bath for 2 hours. The mass was re-suspended occasionally with a spatula.

The digested guar was recovered by filtration and rinsed with methanol to remove HCl. The filtrate was light red. The product was dried overnight at 70 degrees Celsius under 24" Hg vacuum with nitrogen purge. 40.4 grams of off-white, free-flowing powder product was recovered.

In the alkylation reaction, 80 grams of deionized water and 10 grams of 2.5 N NaOH were combined in a beaker equipped with a stir bar. The beaker was placed on a stirring hotplate and heat applied. When the temperature reached 55 degrees Celsius, heating was terminated and 10 grams of the hydrolyzed guar was added in increments over about 10 minutes with vigorous stirring. The solution was yellow and somewhat viscous, but homogeneous. 9.0 grams of GTAC was added and the mixture transferred to a round-bottom flask equipped with a stir bar. The flask was sealed with a stopper and the mixture was allowed to react with stirring in a 60 degrees Celsius oil bath for 7 hours. 93.4 grams of a mildly viscous homogeneous solution was recovered. The product solution was designated "G90".

A second batch was prepared by the same procedure, but using only 6.0 grams of GTAC and an overnight stir (15 hours). 95.0 grams were recovered. This batch was designated "G60".

Example 14

This example describes a method for providing a cross-linked cationic guar gum by treatment of a non-cross-linked cationic guar gum with a cross-linking agent, phosphoryl chloride ($POCl_3$). Other suitable cationic functionalization agents which are useful in analogous reactions include, but are not limited to, diglycidyl polyethylene glycol (PEG), diglycidyl bisphenol A, and diglycidyl 1,4-butanediol, oxalyl chloride, phthaloyl chloride, and adipoyl chloride.

In this example, the cationic guar gum from Example 13 is cross-linked by reaction with $POCl_3$. The solutions were estimated to be 10% guar gum (not counting the cationic substituents). 50 or 55 grams of a 2.0% solution of Tween 80 in limonene was transferred to a 4-ounce jar, the jar was wrapped with heating tape, and the temperature controller set to 75 degrees Celsius with agitation using the Turrax during heat-up and the reaction. 10 grams of the cationic guar gum solution, equivalent to 1.0 gram guar gum, was added during the beginning of the heat-up. A 0.5% solution of $POCl_3$ in limonene was added when the temperature reached 71 degrees Celsius, and the mixture was agitated at 10,000 rpm for 20 minutes while maintaining a temperature of 75±1 degrees Celsius. The mixture was transferred immediately to a separatory funnel. A somewhat viscous lower aqueous phase separated over about a minute and was isolated. Separation was faster for guar gums with a higher degree of cross-linking. 20 milliliters of absolute ethanol was added, leading to precipitation of the product. After standing for 15 minutes, the suspension was filtered with a coarse Buchner funnel and rinsed with ethanol. A white solid was recovered and dried overnight at 50 degrees Celsius under 24" Hg vacuum with nitrogen purge. Recoveries are shown in Table 20. The products crushed easily to a fine powder. A little of the product was dispersed in water. The G90 particles hydrated in about 5 minutes, the G60 particles hydrated in about 20 minutes. All particles remained well dispersed after hydration and did not readily settle.

TABLE 20

| Batch | Cationic guar gum | $POCl_3$:cationic guar gum | $POCl_3$ | Yield |
|---|---|---|---|---|
| G90_5P Batch 1 | G90 | 5% | 10 g | 0.27 g |
| G90_5P Batch 2 | G90 | 5% | 10 g | 0.64 g |
| G90_2P | G90 | 2% | 4 g | 0.38 g |
| G90_8P | G90 | 8% | 16 g | 0.67 g |
| G60_5P | G60 | 5% | 10 g | 0.48 g |
| G60_2P | G60 | 2% | 4 g | 0.67 g |
| G60_8P | G60 | 8% | 16 g | 0.60 g |

Example 15

This example describes a method for providing a cross-linked cationic guar gum by treatment of a non-cross-linked cationic guar gum with a cross-linking agent, diglycidyl ethers. Other suitable cationic functionalization agents which are useful in analogous reactions include, but are not limited to, diglycidyl polyethylene glycol (PEG), diglycidyl bisphenol A, and diglycidyl 1,4-butanediol, oxalyl chloride, phthaloyl chloride, and adipoyl chloride.

In this example, the cationic guars from Example 13 were converted to cationic cross-linked guar gum particles using diglycidyl ethers as the cross-linking agent. The diglycidyl ethers used were polyethylene glycol diglycidyl ether $M_n$ 500, polyethylene glycol diglycidyl ether $M_n$ 6000, 1,4-butanediol diglycidyl ether, and bisphenol diglycidyl ether. The two polyethylene glycol diglycidyl ethers are long, hydrophilic cross-linkers while the more hydrophobic 1,4-butanediol diglycidyl ether and bisphenol A diglycidyl ether are intermediate in cross-linking length between the polyethylene glycol diglycidyl ethers and phosphoryl chloride.

10 grams of cationic guar solution from Example 13 (equivalent to 1 grams of guar gum) was combined with an amount of cross-linker. As soon as possible thereafter, the guar gum/cross-linker solution was added to 55 grams of 2% Tween 80 in limonene in a 4-ounce jar. The jar was wrapped with heating tape and the temperature controller set to 70 degrees Celsius with agitation at 10,000 rpm using a Turrax during heat-up and the reaction. After 45 minutes, 10 milliliters of water were added to compensate for evaporation. Agitation and heating were continued. 80 minutes into the reaction, 5 milliliters of water were added and heating was terminated. After 10 further minutes of agitation (90 minute total reaction time), the mixture was transferred to a separatory funnel. The mixture promptly separated into two phases. The lower (aqueous) phase was isolated. The product was precipitated by addition of two 10-milliliter aliquots of absolute ethanol. After standing for 15 minutes, the product was collected by filtration, rinsed with ethanol, and dried overnight at 50 degrees Celsius under 24" Hg vacuum with nitrogen purge. The product was then crushed to a fine powder with a mortar and pestle. When added to water, all products hydrated over about 15 minutes. The particles were picked up in water almost immediately and gradually swelled. Dispersion and settling behaviour are noted in Table 21. The cationic guar gum particles that were cross-linked with polyethylene glycol diglycidyl ether $M_n$ 500, polyethylene glycol diglycidyl ether $M_n$ 6000, 1,4-butanediol diglycidyl ether, and bisphenol diglycidyl ether were denoted with the suffix "PGA," "PGB," "BD", and "BP", respectively.

TABLE 21

| Batch | Cationic Guar Gum | Cross-linker | Cross-linker amount | Yield | Settles? |
|---|---|---|---|---|---|
| G60_45PGA | G60 | polyethylene glycol diglycidyl ether $M_n$ 500 | 0.45 g | 0.66 g | No |
| G90_45PGA | G90 | polyethylene glycol diglycidyl ether $M_n$ 500 | 0.45 g | 0.64 g | No |
| G90_25PGB | G90 | polyethylene glycol diglycidyl ether $M_n$ 6000 | 0.25 g | 0.69 g | Yes |
| G60_5BP | G60 | 1,4-butanediol diglycidyl ether | 0.05 g | 0.67 g | Yes |
| G60_10BD | G60 | bisphenol diglycidyl ether | 0.10 g | 0.60 | No |

Example 16

This example describes a method for providing a cross-linked cationic guar gum by treatment of an enzymatically digested guar gum with glycidyltrimethylammonium chloride (GTAC), and polyethylene glycol diglycidyl ether $M_n$ 500. Other suitable cationic functionalization agents which are useful in analogous reactions include, but are not limited to, 2,3-epoxypropyl-N,N,N-trimethylammonium chloride, 3-chloro-2-hydroxypropyl-N,N,N-trimethylammonium chloride, 3-chloro-2-hydroxypropyl-N,N,N-dimethylethanolammonium chloride, 2,3-epoxypropyl-N,N,N-trimethylammonium chloride, and 1,3-bis-(3-chloro-2-hydroxypropyl-N,N-dimethylammonium)-N-propane dichloride. Other suitable cationic functionalization agents which are useful in analogous reactions include, but are not limited to, diglycidyl polyethylene glycol (PEG), diglycidyl bisphenol A, and diglycidyl 1,4-butanediol, oxalyl chloride, phthaloyl chloride, and adipoyl chloride.

In this example, 33.6 grams of Sunfiber® enzymatically hydrolyzed guar gum (Taiyo International, Inc., 5960 Golden Hills Drive, Minneapolis, Minn. 55416) was gradually added to 100 milliliters of deionized water over about 30 minutes at room temperature. Dissolution was almost complete. 30.2 grams of GTAC (90 wt % with respect to guar gum) and 2.0 grams of 50% NaOH were added and the mixture was stirred briefly, capped, transferred to a 60 degrees Celsius oil bath, and stirred overnight (17 hours). The overall nominal concentration of guar gum was 20.3% in the solution. 163.4 grams of dark red-brown homogeneous liquid was recovered.

The cationic guar was cross-linked with polyethylene glycol diglycidyl ether $M_n$ 500. Cross-linker levels of 25% and 45% were used, designated GS90_25 PGA and GS90_45PGA. 20 grams of the cationic guar solution, equivalent to 4 grams of unmodified guar, was combined with polyethylene glycol diglycidyl ether $M_n$ 500 and immediately added to 110 grams of 2% Tween 80 in limonene in an 8-ounce jar. The jar was wrapped with heating tape and the temperature controller set to 70 degrees Celsius with agitation at 10,000 rpm using a Turrax during heat-up and the reaction. After 45 minutes, 15 milliliters of water were added to compensate for evaporation. Agitation and heating continued. 75 minutes into the reaction, 10 milliliters of water were added and heating was terminated. After brief stirring, the mixture was transferred to a separatory funnel. The mixture separated into two phases over about 15 minutes.

The lower (aqueous) phase was isolated and 35 milliliters of absolute ethanol were added all at once. The mixture was swirled, leading to separation of the product as a soft, colorless material. The product tended to agglomerate. It was broken up with a spatula, still in suspension, and allowed to stand for 15 minutes before recovering the product by filtration in a Buchner funnel. Filtration was rapid. The colorless, light, fluffy powder was rinsed with ethanol and dried overnight at 60 degrees Celsius under 24" Hg vacuum with nitrogen purge. Yields are provided in Table 22. The products were crushed with ease using a mortar and pestle. A small amount of the particles was combined with deionized water. Both products dissolved virtually instantly yielding clear solutions.

TABLE 22

| Batch | Cross-linker amount | Yield |
|---|---|---|
| GS90_25PGA | 1.0 g | 2.20 g |
| GS90_45PGA | 1.8 g | 2.43 g |

Example 17

This example describes cationic functionalization and cross-linking of cationic corn starch and acid-digested guar gum with adipoyl chloride, a flexible linker. Cationic polysaccharides that are cross-linked with longer or more flexible cross-linkers may improve accommodation of polynucleotides such as double-stranded RNAs.

In this example, cationic guar solution G90 from Example 13 was used along with fresh batches of cationic corn starch C56 and C70 prepared by a method similar to that described in Example 1. In a 1-liter round-bottom flask equipped with a stir bar, 20 grams of corn starch (unmodified waxy corn starch of essentially pure amylopectin) were dissolved in 25 grams of 2.5 N NaOH plus 450 milliliters of water. Glycidyltrimethylammonium chloride (GTAC) (>90%), was added and the mixture was stirred overnight, uncapped in a 60 degrees Celsius oil bath. Results are provided in Table 23.

TABLE 23

| Reaction | GTAC:Starch | GTAC | Mass Recovered | Reaction time |
|---|---|---|---|---|
| C56 | 56% | 11.2 g | 463 g | 16 h |
| C70 | 70% | 14.0 g | 487 g | 6 h |

1% solutions of Tween 80 in limonene and of adipoyl chloride in limonene were prepared. 130 grams of the 1.0% Tween 80/limonene solution were transferred to an 8-ounce jar. The jar was wrapped with heating tape and the temperature controller set to 70 degrees Celsius with agitation using the Turrax during heat-up and the reaction. About 24 grams of the cationic starch solution, equivalent to 1.0 grams starch, was added during the beginning of the heat-up. The adipoyl chloride/limonene solution was added when the temperature reached 70 degrees Celsius, and the mixture was agitated at 10,000 rpm for 20 minutes while maintaining a temperature of 70±1 degrees Celsius. The mixture was then immediately poured into a separatory funnel. The product was recovered by addition of absolute ethanol to the aqueous (lower) phase. A gummy mass formed, which was recovered by filtration. In addition to the starch solutions, 10 grams of cationic acid-treated guar G90 from Example 13 was used with the same protocol. The aqueous phase from the G90_6A prep was somewhat viscous and tended to adhere to the walls of the filter flask, and took a few minutes to settle. Unlike the starch-based particles, the product precipitated easily after ethanol addition, yielding a fluffy particle mass. All products were dried overnight at 60 degrees Celsius under 24" Hg vacuum with nitrogen purge. The products were easily crushed in a mortar and pestle The particles were designated by a system similar to that used for particles cross-linked with phosphoryl chloride except that an "A" was appended to indicate that adipoyl chloride was used as the cross-linker. Results are provided in Table 24.

TABLE 24

| Batch | Starch | adipoyl chloride:starch | adipoyl chloride | Recovery | Yield |
|---|---|---|---|---|---|
| C70_2A | 24.4 g | 2% | 2 g | 40 milliliters EtOH | 0.54 g |
| C70_4A | 24.4 g | 4% | 4 g | 30 milliliters EtOH | 0.67 g |
| C56_5A | 23.2 g | 5% | 5 g | 30 milliliters EtOH | 0.20 g |
| G90_6A | 10.0 g | 6% | 6 g | 30 milliliters EtOH | 0.78 g |

Example 18

This example describes an embodiment of a composition including a cationic guar gum and a polynucleotide. More specifically, this example provides a non-limiting embodiment of a solid formulation including a cationic guar gum, a polynucleotide (dsRNA designed to suppress a target gene of an herbivorous pest), and clay.

In this example, a double-stranded RNA (dsRNA) is recovered or isolated from a 0.5% solution by complexing the dsRNA with two different cationic guar gums, Hydroxypropyl cationic guar, mol. wt. approximately 2 million Dalton (guar gum, 2-hydroxypropyl 2-hydroxy-3-(trimethylammonio)propyl ether, chloride), hereinafter "Guar 1" and Cationic guar, degree of substitution approximately 12%, mol. wt. approximately 0.5 million Dalton (guar gum, 2-hydroxypropyl 2-hydroxy-3-(trimethylammonio)propyl ether, chloride), hereinafter "Guar 2"; addition of polyvinyl pyrrolidone, which has a high affinity for clay, releases the RNA-cationic guar agglomerates from the clay.

The dsRNA used in these experiments was a ~800-base-pair blunt-ended dsRNA designed to suppress a target gene of Colorado potato beetle (*Leptinotarsa decemlineata*), a common plant pest. A 22.2 g/L (2.22%) aqueous solution of the dsRNA was diluted to a concentration of 0.5% by combining 22.7 grams of the dsRNA solution with 0.3 grams of an aqueous 39% solution of the tetrasodium salt of ethylenediaminetetraacetic acid, $Na_4EDTA$, made up to 100 milliliters with water. A fresh bottle of bentonite was used.

Three protocols were tested. In each case, 20 grams of the 0.5% dsRNA solution (100 milligrams dsRNA) was added to an Ehrlenmeyer flask equipped with a stir bar. A solution of cationic linear or cross-linked guar was added and the mixture was stirred for 30 minutes to bind and equilibrate. For the protocols using clay, the a slurry of the clay was prepared in 50 milliliters of water and stirred for 10 minutes to hydrate prior to use. The amounts of each component are shown in Table 25.

TABLE 25

| Protocol | Cationic guar | Guar | Clay | RNA:Guar:Clay ratio |
|---|---|---|---|---|
| 737_SAM_4 | Guar 1 | 40 g, 1.0% | 2.0 grams | 1:4:20 |
| 496_SAM_4 | Guar 2 | 28.6 g, 1.4% | 2.0 grams | 1:4:20 |
| 496_SAM_15 | Guar 2 | 28.6 g, 1.4% | 1.3 grams | 1.5:6:20 |

After dsRNA-cationic guar solution was mixed for 30 minutes, the clay slurry was added, and the mixture stirred for five minutes and allowed to stand for 1-10 minutes. The resulting suspensions were filtered through coarse 60-milliliter Buchner funnels. Filtration of 496_SAM_15 was very fast, indicating tighter flocculation of the dsRNA-cationic guar-clay mixture. Vacuum filtration of the other two formulations was continued for 90 minutes and the material remaining in the filter, which still contained liquid, was used in the next (re-dispersion) step.

The entire filter cake was transferred to a 250 milliliter Ehrlenmeyer flask and made up to 50 grams (496_SAM_15) or 200 grams (737_SAM_4 or 496_SAM_4) with 0.4% Sokalan K-17P PVP solution. The 496_SAM_15 suspension was nominally 2 g/L dsRNA; the 737_SAM_4 and 496_SAM_4 formulations were nominally 0.5 g/L dsRNA. In the case of the 737_SAM_4 and 496_SAM_4 formulations, the clays were allowed to settle and a sample of the supernatant was obtained for rainfastness and diet assays; 496_SAM_15 was filtered because of the small amount of liquid and the filtrate used for assays. A clear filtrate was observed for all three formulations, indicating that all were successful in recovering the dsRNA/cationic guar from the solution.

Example 19

This example describes an embodiment of a composition including a cationic guar gum and a polynucleotide. More specifically, this example describes improved rainfastness and pest-control efficacy of dsRNA/cationic guar gum compositions.

Various compositions including dsRNA and cationic guar gum, prepared using treatment with clay and PVD as described in Example 18, were tested using a whole plant infestation assay. Also tested were solutions of the same cationic guar gums added directly to a solution of the dsRNA.

In brief, the whole plant infestation assay was carried out as follows: Tomato or potato plants were seeded in growth chambers for 2 weeks to reach a growth height of ~6 inches. The test compositions were prepared immediately prior to treatment and were applied to the plants at 0.25 micrograms per milliliter (equivalent to 0.03 gram/acre) at a rate equivalent to 30 gallons per acre using a pressurized track sprayer. After overnight acclimation in the growth chamber, moderate rain (0.25 inches) was simulated via a pressurized track sprayer. The control ("pre-rain") and rain simulated ("post-rain) set of plants were then caged and infested with Colorado potato beetle larvae, and returned to growth chambers. Harvesting and scoring of the plants for defoliation and insect counts were analyzed ~14 days post infestation. Results are provided in Table 26 Enhanced rainfastness and improved pest control was observed with the formulation 737_SAM_4/Guar 1+dsRNA.

TABLE 26

| Tank Mix Formulation | Rain Treatment | % Defoliation |
|---|---|---|
| 1% Tween 85 | NA | 58% |
| dsRNA 0.25 micrograms/milliliter + 1% Tween 85 | pre-rain | 9% |
| dsRNA 0.25 micrograms/milliliter + 1% Tween 85 | post-rain | 21% |
| Guar 1 + dsRNA | pre-rain | 12% |
| Guar 1 + dsRNA | pre-rain | 9% |
| 737_SAM_4/Guar 1 + dsRNA | pre-rain | 26% |
| 737_SAM_4/Guar 1 + dsRNA | post-rain | 29% |
| Guar 2 + dsRNA | pre-rain | 16% |
| Guar 2 + dsRNA | post-rain | 63% |
| 496_SAM4/Guar 2 + dsRNA | pre-rain | 65% |
| 496_SAM4/Guar 2 + dsRNA | post-rain | 29% |
| 496_SAM_15/Guar 2 + dsRNA | pre-rain | 64% |
| 496_SAM_15/Guar 2 + dsRNA | post-rain | 68% |

Example 20

This example describes an embodiment of a composition including a cationic guar gum and a polynucleotide provided as solid formulations which disperse readily in water. This example also provides rainfastness data for these formulations.

Solid formulations were prepared incorporating Hydroxypropyl cationic guar, mol. wt. approximately 2 million Dalton (guar gum, 2-hydroxypropyl 2-hydroxy-3-(trimethylammonio)propyl ether, chloride) hereinafter "Guar 1" and Cationic guar, degree of substitution approximately 12%, mol. wt. approximately 0.5 million Dalton (guar gum, 2-hydroxypropyl 2-hydroxy-3-(trimethylammonio)propyl ether, chloride) hereinafter "Guar 2", both of which successfully recovered RNA from solution. The polynucleotide used was the ~800-base-pair blunt-ended dsRNA, see Example 18. An additional dsRNA obtained from E. coli expression was also tested; the E. coli culture was heat-killed, lysed, spun, and then thawed/processed.

The formulations included a small amount of a stabilizer solution consisting of 0.05 grams of the antimicrobial Proxel GXL (1,2-benzisothiazolin-3-one), 0.20 grams of the photostabilizer Maxgard 1800 (benzophenone-9, disodium 2,2'-dihydroxy-4,4'-dimethoxy-5,5'disulfobenzophenone) and 1 gram of an aqueous 39% solution of the tetrasodium salt of ethylenediaminetetraacetic acid, $Na_4EDTA$ made up to 5 grams with deionized water, and stirred to dissolve. 0.1 grams of this mixture was added to each formulation.

The solid formulations were prepared generally as follows: Mixtures of cationic guar solutions, deionized water, and the dsRNA solutions were prepared in 125 milliliter Ehrlenmeyer flasks and stirred for 25 minutes; the mixtures generally were cloudy within the first minute, with minimal cloudiness observed for the Guar 1/E. coli lysate experiment. Aqueous suspensions of bentonite (montmorillonite clay) were also stirred during this time. The two mixtures were then combined and stirred for five minutes. Additional guar solution was added and the mixture stirred gently for 15 minutes. The suspension was vacuum filtered in a 60 milliliter Buchner funnel with a coarse frit for 40 minutes, to mimic filter cake drying in industrial equipment. The supernatant was decanted from the Buchner funnel after 30 minutes for Guar 2/E. coli lysate and after 60 minutes for Guar 1/E. coli lysate and the filtration time extended to 2.0 and 2.5 hours respectively. The final filter cake had a rubbery texture for Guar 2/E. coli lysate and was a thick liquid for Guar 1/E. coli lysate. The filter cakes were transferred to a ceramic mortar and weighed. 50% gluconic acid, followed by Armeen DMOD and Pluronic F108 were added and mixed in with a spatula, leading to dramatic softening of the filter cake. Other formulation components included Armeen DMOD (distilled dimethyl oleyl amine), Pluronic F108 (equivalent to poly(ethylene glycol)-block-poly(propylene glycol)-block-poly(ethylene glycol), average $M_n$~14,600), Finnfix 2, a low molecular weight sodium carboxymethyl cellulose, Aerosil 200, a fumed silica, and kaolin. These additional components were added in order, as described in detail below.

The specific compositions for preparing each solid formulation are as follows:

1. Guar 2 formulations, 2.7% RNA (dry basis)
   Guar-RNA Mixture
   10.7 grams 1.4% Guar 2 solution (150 milligrams guar)
   2.5 grams synthesized dsRNA or 12.8 grams dsRNA in E. coli lysate (50 milligrams RNA)
   25 milliliters deionized water
   Clay Suspension
   0.6 grams bentonite
   25 milliliters deionized water
   Additional Guar Solution
   3.5 grams 1.4% Guar 2 solution (50 milligrams guar)
   0.16 grams 50% gluconic acid
   0.12 grams Armeen DMOD
   0.1 grams Pluronic F108
   0.1 grams stabilizer solution
   0.2 grams kaolin clay
   0.5 grams Finnfix 2

2. Guar 1 formulation with synthesized dsRNA, 3.0% RNA (dry basis)
   Guar-RNA Mixture
   20 grams 1.0% Guar 1 solution (200 milligrams guar)
   3.8 grams synthesized dsRNA, approximately equal to 75 milligrams RNA
   20 milliliters deionized water
   Clay Suspension
   0.4 grams bentonite
   25 milliliters deionized water
   Additional Guar Solution
   3 grams 1.0% Guar 1 solution (30 milligrams guar)
   Added to the Mortar (in Order of Addition)
   0.18 grams 50% gluconic acid
   0.13 grams Armeen DMOD
   0.08 grams Pluronic F108
   0.1 grams stabilizer solution
   0.5 grams kaolin
   0.1 grams Aerosil 200
   0.9 grams Finnfix 2

3. Guar 1 formulation for dsRNA in E. coli lysate, 2.4% RNA (dry basis, neglecting RNA loss in filter)
   Guar-RNA Mixture
   20 grams 1.0% Guar 1 solution (200 milligrams guar)
   15.3 grams E. coli lysate, approximately equal to 60 milligrams RNA)
   20 milliliters deionized water
   Clay Suspension
   0.4 grams bentonite
   25 milliliters deionized water
   Additional Guar Solution
   3 grams 1.0% Guar 1 solution (30 milligrams guar)
   Added to the Mortar (in Order of Addition)
   0.22 grams 50% gluconic acid
   0.16 grams Armeen DMOD
   0.08 grams Pluronic F108
   0.1 grams stabilizer solution 0.3 grams kaolin
0.3 grams Aerosil 200
0.7 grams Finnfix 2

The formulations were dried overnight at 30 degrees Celsius under 24" Hg vacuum with nitrogen purge. They were then crushed in a mortar and pestle. The formulations were dry and hard, but a little resinous, and crushed to flakes and coarse powder. All formulations dispersed well in water. Dispersion of the Guar 2 formulations was faster than the Guar 1 formulations.

The dry formulations were rehydrated and the resulting solutions sprayed outdoors on potato plants. Solutions of synthesized dsRNA and dsRNA in *E. coli* lysate in 1% Tween 85 surfactant were sprayed as controls. The mean polynucleotide amount detected on the sprayed leaves immediately after spraying and at various times after spraying are provided in Table 27. Formulations incorporating Guar 1 cationic guar gum dramatically improved outdoor stability and retention of the polynucleotides compared to the polynucleotides applied as Tween 85 solutions or in Guar 2 formulations.

TABLE 27

| Formulation | Amount of dsRNA applied* | Time after spraying 0 h | 24 h | 48 h | 72 h | 144 h |
|---|---|---|---|---|---|---|
| synthesized dsRNA/Tween | 431 | 100.0% | 55.6% | 20.3% | 22.6% | 5.0% |
| synthesized dsRNA/Tween | 431 | 100.0% | 46.0% | 29.6% | 25.4% | 2.8% |
| synthesized dsRNA/ Guar 2 solid formulation | 484 | 100.0% | 93.6% | 30.0% | 26.4% | 7.5% |
| synthesized dsRNA/ Guar 1 solid formulation | 234 | 100.0% | 109.1% | 98.6% | 60.1% | 98.8% |
| *E. coli* lysate/ Tween | 290 | 100.0% | 39.6% | 53.7% | 20.1% | 5.4% |
| *E. coli* lysate/ Tween | 289 | 100.0% | 48.2% | 16.7% | 29.5% | 12.1% |
| *E. coli* lysate/ Guar 2 solid formulation | 250 | 100.0% | 88.0% | 27.1% | 15.9% | 7.4% |
| *E. coli* lysate/ Guar 1 solid formulation | 124 | 100.0% | 41.0% | 21.3% | 27.0% | 21.1% |

*nanogram dsRNA per microgram total RNA measured with a Quantigene assay

Example 21

This example describes preparation of dry formulations including a polynucleotide and cationic guar gum, and further including a silicate. More specifically, this example describes a formulation including dsRNA, cationic guar gum, and sodium montmorillonite clay, wherein the formulation displays rapid dispersion in water.

Compositions including a polynucleotide and cationic guar gum were prepared using procedures similar to those described in Example 20. Instead of Armeen DMOD, Ethomeen® C/15, a polyoxyethylene (5) cocoalkylamine (TSCA number 61791-14-8 from Akzo Nobel, 13295 Lakefront Dr, Earth City, Mo. 63045, also available as catalogue number P2994, CAS 61791-14-8, from Spectrum Laboratory Products, Inc., 14422 S. San Pedro St., Gardena, Calif. 90248) was used as it is classified as an EPA inert. In some formulations, Ultrazine NA, a sodium lignosulfonate dispersant was also used. A 1.0% solution of Guar 1 and a 1.4% solution of Guar 2 were used. The polynucleotide/cationic guar gum formulations were prepared with these formulations:

1. Guar 2 Formulations

| | |
|---|---|
| 50% gluconic acid | 0.19 g |
| Ethomeen ® C/15 | 0.21 g |
| Reax 907 | 0.10 g |
| Kaolin | 0.30 g |
| Emulpon CO-550 | 0.25 g |
| Finnfix 2 | 0.40 g |
| Aerosil 200 | 0.10 g |

2. Guar 1 Formulations

| | |
|---|---|
| 50% gluconic acid | 0.10 g |
| Ethomeen ® C/15 | 0.10 g |
| Ultrazine NA | 0.10 g |
| Kaolin | 0.20 g |
| Emulpon CO-550 | 0.4 g |
| Finnfix 2 | 0.20 g |
| Aerosil 200 | 0.15 g |

The formulations were prepared using two dsRNAs (~900 base-pair "dsRNA B" and ~900 base-pair "dsRNA C"), which were produced in *E. coli* and provided as the clarified microbial lysate. For some formulations, ~800 base-pair blunt-ended dsRNA "dsRNA A" was added as a 0.5% solution stabilized with $Na_4EDTA$, in amounts providing 50 milligrams of dsRNA for the Guar 2 formulations and 75 milligrams for Guar 1 formulations.

Filter cakes were prepared by the procedure in Example 20 with adjustments for the concentration of dsRNA in the lysate. Lysate, cationic guar solution, and deionized water were combined in an Ehrlenmeyer flask and stirred for 25 minutes, forming cloudy solutions with no visible particles. Meanwhile, bentonite (montmorillonite clay) was stirred to disperse in water in a small Ehrlenmeyer. After the lysate-cationic guar mixture had stirred for 25 minutes, the clay suspension was added and stirred for five minutes. More cationic guar solution was added and the mixture stirred for another 15 minutes. Flocculation occurred within seconds of the second guar addition in all cases. The resulting suspension was vacuum filtered for at least 40 minutes in order to dry the filter cake. Compositions of the different formulations are provided in Table 28.

TABLE 28

| Initial guar amount | synthesized dsRNA A | Lysate dsRNA | deionized $H_2O$ | Clay/$H_2O$ | $2^{nd}$ guar addition |
|---|---|---|---|---|---|
| Guar 2, 10.7 g | 10.0 grams 0.5% | — | 10.0 g | 0.6 g/25 milliliters | 0.6 g/25 milliliters |
| Guar 2, 10.7 g | 10.0 grams 0.5% | "dsRNA B": 8.2 g | 11.8 g | 0.6 g/25 milliliters | 0.6 g/25 milliliters |
| Guar 2, 10.7 g | 10.0 grams 0.5% | "dsRNA C": 13.2 g | 6.8 g | 0.6 g/25 milliliters | 0.6 g/25 milliliters |
| Guar 1, 20 g | 15.0 grams 0.5% | — | 15.0 g | 0.4 g/25 milliliters | 3 g |
| Guar 1, 20 g | 15.0 grams 0.5% | "daRNA B": 12.2 g | 17.8 g | 0.4 g/25 milliliters | 3 g |
| Guar 1, 20 g | 15.0 grams 0.5% | dsRNA C": 19.7 g | 10.3 g | 0.4 g/25 milliliters | 3 g |

The filter cakes were transferred to a mortar. The formulation components below were mixed into the filter cake with a spatula, but a pestle was used to mix in the kaolin. The formulations were transferred to glass jars and dried overnight at 30 degrees Celsius under 24" Hg vacuum with nitrogen purge. The dry formulations were crushed in a mortar and pestle. All formulations were hard after drying and dispersed rapidly in water.

Example 22

This example describes preparation of dry formulations including a polynucleotide and cationic guar gum, and further including a silicate. More specifically, this example describes use of dispersant agents in preparing a formulation including dsRNA and cationic guar gum.

Experiments with various dispersant agents were carried out. In a set of experiments, dimethyldistearyl ammonium chloride (DMDS, an EPA inert) was used as a release agent to displace Guar 2 cationic guar gum complexed to the polynucleotide dsRNA from the surface of montmorillonite clay. The DMDS formulations were successful in dispersing the cationic guar gum/polynucleotide from the clay, but some undesirable lumps of clay remained after dispersion in water. Experiments using dimethyloleylamine protonated with gluconic acid produced complete dispersion using a different cationic guar, Guar 1. Experiments were carried out with Ethomeen® C/15, a polyoxyethylene (5) cocoalkylamine.

Filter cakes were prepared by similar procedures as those described in Example 21. A 0.5% solution of dsRNA was used and fresh solution prepared as required. 22.5 grams of a solution of dsRNA, 22.2 g/L (2.22%) was combined with 0.2 grams of Versene 100 and made up to 100 g with deionized water. A 1.4% solution of Guar 2 cationic guar solution was prepared as needed by adding 8.4 grams of the guar to 600 milliliters of warm water maintained at 55 degrees Celsius with vigorous stirring over 32 minutes. These solutions were used to produce filter cakes of 1:4:12 dsRNA/Guar 2 cationic guar/montmorillonite clay as follows: 10.7 grams of a 1.4% Guar 2 solution (150 milligrams guar) were combined with 10.0 grams of the 0.5% solution of RNA and 10 milliliters of deionized water in a 125 milliliter Ehrlenmeyer flask equipped with a stir bar. The mixture was stirred for 25 minutes. Meanwhile, a mixture of 0.6 grams of bentonite (montmorillonite clay) and 25 milliliters of water was stirred to hydrate and suspend the clay. The clay and guar-dsRNA solutions were combined and stirred for five minutes. No flocculation occurred. 3.5 grams of the 1.4% Guar 2 solution (50 milligrams guar) was added and stirred slowly for 15 minutes, allowing time for the newly-added cationic guar to bind the dsRNA. The filter cake was recovered by vacuum filtration and transferred to a small mortar where it was weighed. The vacuum filtration time was extended to 40 minutes in order to mimic industrial scale cake drying.

Two Guar 2 cationic guar gum formulations were prepared initially by transferring the filter cakes to a mortar and adding the other components of the formulation in the order shown in Table 29. The amounts of Finnfix 2 and Aerosil 200 fumed silica were adjusted to ensure that the resulting dough-like solids were extrudable. Kaolin was ground in with the pestle to break up clusters of montmorillonite.

TABLE 29

| Component | Formulation 1 | Formulation 2 |
|---|---|---|
| 50% gluconic acid | 0.19 g | 0.15 g |
| Ethomeen ® C/15 | 0.21 g | 0.16 g |
| Ufoxane Ultra CA | 0.1 g | 0.1 g |
| Kaolin | 0.3 g | 0.3 g |
| Emulpon CO-550 | 0.4 g | 0.2 g |
| Finnfix 2 | 0.5 g | 0.5 g |
| Aerosil 200 | 0.15 g | 0.1 g |

The doughs were transferred to weighing boats and allowed to dry under ambient conditions overnight. Both Formulation 1 and 2 were hard enough for a pellet after air-drying but somewhat crumbly. Samples of the two formulations were placed in vials containing 10 milliliters of deionized water. Dispersion behaviour is described in Table 30.

TABLE 30

| Formulation | Filter cake | Before drying | After drying | Hardness | Dispersion |
|---|---|---|---|---|---|
| 1 | 3.4 g | 3.8 g | 2.2 g | Very hard | Rapid initial disintegration to very fine particles, near-complete in 10 minutes. Formed cloudy supernatant that was stable for hours. |
| 2 | 3.2 g | 3.4 g | 1.9 g | Very hard, smooth | Rapid initial disintegration to fine particles. Proceeded steadily. |

Further experiments were carried out to adjust the various components used in the formulations. In a set of experiments, the lignosulfonate dispersants were adjusted. Two lignosulfonates, Reax 907 and Kraftsperse 25M (both obtained from Mead Westvaco) were evaluated alongside the modified sodium lignosulphonate sold as Ufoxane Ultra CAused in Formulations 1 and 2. Like Ufoxane, Reax 907 and Kraftsperse 25M have a high molecular weight; Reax 907 has a low level of sulfonation (1.2 mol $SO_3$/kg); Kraftsperse 25M has higher sulfonation (2.9 mol $SO_3$/kg). In one experiment, 0.1 grams of glycerol monostearate (Alfa Aesar) was added at the same time as Ufoxane Ultra CA in order to create a more hydrophobic montmorillonite to improve dispersion. A base mixture used was similar to Formulation 1 but contained:

| | |
|---|---|
| 50% gluconic acid | 0.19 g |
| Ethomeen ® C/15 | 0.21 g |
| Lignosulfonate | 0.1 g |
| Kaolin | 0.3 g |
| Emulpon CO-550 | 0.25 g |
| Finnfix 2 | 0.4 g |
| Aerosil 200 | 0.1 g |

The components added to this base mixture for different formulations were added in the order shown in Table 31.

TABLE 31

| Formulation | Lignosulfonate | Filter cake | Notes |
|---|---|---|---|
| 3 | Ufoxane | 2.9 g | Good tough dough, would extrude well |
| 4 | Kraftsperse 25M | 3.0 g | Dough was a bit too soft, darker. |
| 5 | Reax 907 | 3.5 g | Dough too soft, probably due to cake moisture |

TABLE 31-continued

| Form-ulation | Lignosulfonate | Filter cake | Notes |
|---|---|---|---|
| 6 | Ufoxane/0.1 grams glycerol monostearate | 2.8 g | GMS softened dough a little, but final dough was smooth and tough with perfect rheology |

After air-drying overnight, all four formulations had good rheology: hard, but slightly crumbly. Dispersion behaviour is described in Table 32.

TABLE 32

| Form-ulation | Before drying | After drying | Hardness | Dispersion |
|---|---|---|---|---|
| 3 | 3.1 g | 1.7 g | Excellent | Very fast initial disintegration. Stable, light-colored suspension of fine particles |
| 4 | 3.2 g | 1.9 g | Excellent | Very fast initial disintegration. Less stable fine particle suspension |
| 5 | 3.4 g | 1.9 g | Excellent | Very fast initial disintegration. Good stable suspension of fine particles. Darker colored supernatant and settled particles. |
| 6 | 3.2 g | 1.9 g | Excellent | Very fast initial disintegration. Less stable fine particle suspension |

Dispersion of the formulations in the 10-milliliter vial assay proceeded rapidly, with formulations 3 and 6 somewhat faster than formulations 4 and 5. This may be due to the lower cake moisture of formulations 3 and 6, however. Dispersion of formulations 3 and 5 were nearly complete after 15 minutes with occasional shaking. Formulation 6 had a few stubborn lumps. After standing for 2 hours, the supernatant of formulation 4 was almost clear; the others were still cloudy. Formulation 5 was less cloudy than the Ufoxane-containing formulations 3 and 6, although this may be attributable to cake moisture. Formulations 3 and 6 were the same except for the addition of 0.1 grams of glycerol monostearate to formulation 6. Both started with relatively dry filter cakes. The addition of glycerol monostearate appeared to be slightly detrimental to disintegration. These results indicated that formulations 3 and 5 had superior dispersion behaviour.

Formulations 3 and 5 were re-prepared by the same procedure, but the doughs were dried overnight at 30 degrees Celsius under 24" Hg vacuum with nitrogen purge. Both wet doughs were tough and well-suited for extrusion. The dry formulations were crushed in a mortar and pestle and evaluated in the dissolution assay. Both dispersed very quickly initially and were nearly complete after five minutes. Supernatant from the dissolution tests of formulations 3 and 5 were spread on glass slides and allowed to dry. Both formed indistinguishable, continuous particle films composed of submicron particles studded with fine clay particles.

On a dry basis, the composition of formulations 3 and 5 is given in Table 33:

TABLE 33

| | |
|---|---|
| RNA | 2.17% |
| Guar 2 | 8.63% |
| Bentonite clay | 26.04% |
| Gluconic acid | 4.12% |
| Ethomeen C/15 | 9.12% |
| Lignosulfonate | 4.34% |
| Castor oil ethoxylate | 10.85% |
| Kaolin | 13.02% |
| Finnfix 2 | 17.36% |
| Fumed silica | 4.34% |

This formulation appears exhibit suitable characteristics. The wet dough is tough enough for extrusion and not very sticky. After drying, the formulation is hard enough for a water-dispersable granule, yet dissolves readily with only mild agitation. All of the components are considered EPA inerts. The formulation has a high bulk density and the RNA loading on a volume basis is adequate.

Example 23

This example describes preparation of dry and liquid formulations of compositions including a polynucleotide and cationic guar gum. More specifically, this example describes formulations including dsRNA/cationic guar gum complexes that are useful for foliar spray treatments in the field or greenhouse.

A generic formulation including a dsRNA/cationic guar gum complex is as follows:

| | |
|---|---|
| dsRNA | 0.25% |
| Proxel GXL | 0.05% |
| $Na_4EDTA$ | 0.19% as the salt, (=0.15% as EDTA acid) |
| Water | Balance to make up 100% |

Several formulations were prepared using dsRNA designed to suppress target genes in the flea beetle species *Phyllotreta cruciferae* and *Phyllotreta striolata*. These dsRNA are listed in Table 34.

TABLE 34

| Species | dsRNA |
|---|---|
| *Phyllotreta cruciferae* | D |
| *Phyllotreta cruciferae* | E |
| *Phyllotreta cruciferae* | F |
| *Phyllotreta cruciferae* | G |
| *Phyllotreta cruciferae* | H |
| *Phyllotreta cruciferae* | I |
| *Phyllotreta cruciferae* | J |
| *Phyllotreta cruciferae* | K |
| *Phyllotreta striolata* | L |
| *Phyllotreta striolata* | M |
| *Phyllotreta striolata* | N |
| *Phyllotreta striolata* | O |
| *Phyllotreta striolata* | P |
| *Phyllotreta striolata* | Q |
| Green fluorescent protein, GFP (control) | R |

Three further formulations of dsRNA F are provided below.

TABLE 35

| Formulation F1, liquid formulation of dsRNA F and cationic starch C56_3: | |
|---|---|
| dsRNA F | 0.25% |
| Cationic starch C563 | 2.5% |

TABLE 35-continued

Formulation F1, liquid formulation of dsRNA F and cationic starch C56_3:

| | |
|---|---|
| Proxel GXL | 0.05% |
| Na₄EDTA | 0.19% as the salt, (=0.15% as EDTA acid) |
| Water | Balance |

TABLE 36

Formulation F2, solid formulation of dsRNA and Guar 1:

| Common name | Trade name | Weight % | Purpose |
|---|---|---|---|
| dsRNA | | 3.5% | Insecticide |
| Cationic guar gum | Guar 1 | 10.7% | Sticker |
| Bentonite clay | Volclay HPM 20 | 18.5% | Filler |
| Gluconic acid | Gluconic acid | 2.3% | pH modifier |
| — | Ethomeen C/15 | 4.6% | Dispersant |
| 1,2-benzisothiazolin-3-one | Proxel GXL | 0.05% | Antimicrobial |
| Lignosulfonate | Reax 907 | 4.6% | Dispersant |
| Castor oil ethoxylate | Emulpon CO-550 | 18.5% | Surfactant |
| Kaolin | ASP 900 | 23.2% | Filler |
| Sodium carboxymethyl cellulose | Finnfix 2 | 9.3% | Binder |
| Fumed silica | Aerosil 200 | 4.6% | Filler |

TABLE 37

Formulation F3, solid formulation of dsRNA and Guar 2:

| Common name | Trade name | Weight % | Purpose |
|---|---|---|---|
| dsRNA | | 2.5% | Insecticide |
| Cationic guar gum | Guar 2 | 9.9% | Sticker |
| Montmorillonite clay | Mineral Colloid MO | 19.9% | Filler |
| Gluconic acid | Gluconic acid | 3.2% | pH modifier |
| — | Ethomeen C/15 | 7.0% | Dispersant |
| 1,2-benzisothiazolin-3-one | Proxel GXL | 0.05% | Antimicrobial |
| Lignosulfonate | Ultrazine NA | 7.5% | Dispersant |
| Castor oil ethoxylate | Emulpon CO-550 | 12.5% | Surfactant |
| Kaolin | ASP 900 | 19.9% | Filler |
| Sodium carboxymethyl cellulose | Finnfix 2 | 10.0% | Binder |
| Fumed silica | Aerosil 200 | 7.5% | Filler |

Any of the various compositions including a dsRNA/cationic starch complex or a dsRNA/cationic guar gum complex described here and elsewhere in this description can be applied to plants as a suitable formulation (e. g., as a solid, liquid, powder, suspension, or emulsion) and by any convenient technique including, but not limited to, spraying or soaking or dusting a plant or a part of a plant with the formulation.

In an embodiment, a composition including a dsRNA/cationic starch complex or a dsRNA/cationic guar gum complex is applied as a foliar spray to a plant or part of a plant. Foliar sprays are conveniently prepared as tank mixes by diluting a concentrated liquid formulation or by redissolving or resuspending a dry formulation, with the optional addition of adjuvants to the tank mix. Examples of commercially available adjuvants useful in preparing tank mixes include Tween 85, Silwet L77, Silwet HS-312, Fz-77, BreakThru SP131, BreakThru SP133, BreakThru SP200, 0E441, Silsense A21, alkyl polyglycoside (APG), and Tactic.

In an embodiment, a tank mix is generally prepared by diluting a selected adjuvant into the tank, followed if necessary by addition of a defoaming agent (e. g., 0.05% Agnique defoamer), followed by addition of the liquid or dry formulation containing the dsRNA/cationic starch complex or a dsRNA/cationic guar gum complex; the tank mix is agitated after each component is added to ensure complete dispersion.

In a typical example of a 2-liter tank mix of a formulation to control flea beetles, the tank is filled with half of the total volume (i. e., 1 liter), any required adjuvants are added, the active ingredient ("Formulation F1", liquid formulation of dsRNA and cationic starch C56_3; see Example 23) added according to the final desired concentration as shown in Table 38, and the final volume made up to 2 liters with deionized water.

TABLE 38

| Application Rate (g/acre) | Volume of Formulation F1 (milliliters) per 2 L Spray Volume at 20 gallons/acre |
|---|---|
| 0.2 | 2.11 |
| 0.5 | 5.28 |
| 1 | 10.57 |
| 2 | 21.14 |

For foliar application to control *Phyllotreta cruciferae* on canola plants, optimum application timing is determined by monitoring flea beetle pressure and activity. A first application of the formulation is made when flea beetle damage reaches about 10-15% cotyledon injury. A second application is applied one week later. The Formulation F1 tank mix is applied at a rate of 20 gallons per acre (GPA) using a backpack sprayer equipped with a flat fan nozzle. It is recommended that boom height is minimized to optimize coverage uniformity and maximize deposition by reducing drift. Application of the formulation is made in the morning, within two hours after preparation of the tank mix, and only if rain is not forecast for that day.

Another embodiment is a dry formulation containing the dsRNA/cationic starch complex or a dsRNA/cationic guar gum complex, which is mixed with water prior to foliar application to control *Phyllotreta cruciferae* on canola plants. In an example, the tank mix is sprayed at a dsRNA application rate of 0.2 to 2 g/acre in a single application, or alternatively two sequential sprays are applied one week apart to provide a total dsRNA application rate of 0.4 to 4 g/acre.

What is claimed is:

1. A composition comprising:

a. a cross-linked cationic polysaccharide, and b. a polynucleotide, wherein the polysaccharide is selected from the group consisting of starch and guar gum, wherein the polynucleotide comprises at least 21 contiguous nucleotides that are complementary or identical to a target gene in a pest, wherein the polynucleotide and the cross-linked cationic polysaccharide are bound by electrostatic attraction to form a complex, wherein the complex has at least one dimension that exceeds 200 nanometers or has at least one dimension that exceeds 500 nanometers when hydrated, and wherein the composition exhibits improved rain fastness for the polynucleotide compared with a composition without the cross-linked cationic polysaccharide.

2. The composition of claim 1, wherein the complex is a porous, hydrophilic particle.

3. The composition of claim 1, wherein the complex is non-soluble in an aqueous solution.

4. The composition of claim 1, wherein the composition is provided as an aqueous suspension.

5. The composition of claim 1, wherein the cross-linked cationic polysaccharide comprises one or more cationic functional groups.

6. The composition of claim 5, wherein the one or more cationic functional groups comprises an amine or an ammonium cation.

7. The composition of claim 6, wherein the amine or the ammonium cation
 a). is one or more selected from the group consisting of a primary amine, a secondary amine, a tertiary amine, and a quaternary ammonium cation;
 b). is one or more selected from the group consisting of an optionally substituted amine, a nitrogen-containing heterocyclyl, a quaternary ammonium, and a nitrogen-containing heteroaryl, each of which may be optionally independently substituted with one or more of hydroxyl, alkyl, cycloalkyl, alkenyl, alkoxy, amino, aryl, heterocyclyl, or heteroaryl; or
 c). is one or more selected from the group consisting of —$NH_2$, —$NHR^1$, —$NR^1R^2$, —$NR^1R^2R^3$, and —$N^+R^1R^2R^3R^4$, wherein $R^1$, $R^2$, $R^3$, and $R^4$ are each independently alkyl, each of which may be optionally independently substituted with one or more of hydroxyl, alkyl, alkenyl, alkoxy, amino, aryl, heterocyclyl, or heteroaryl.

8. The composition of claim 1, wherein the cross-linked cationic polysaccharide is provided by reaction of a non-cross-linked polysaccharide with an alkylating agent.

9. The composition of claim 1, wherein the cross-linked cationic polysaccharide is provided by reaction of
 a). a non-cross-linked polysaccharide with diacid chlorides of dicarboxylic acids or with diglycidyl ethers;
 b). a non-cross-linked polysaccharide with phosphoryl chloride ($POCl_3$), diglycidyl polyethylene glycol (PEG), diglycidyl bisphenol A, diglycidyl 1,4-butanediol, oxalyl chloride, phthaloyl chloride, or adipoyl chloride; or
 c). a non-cross-linked starch with glycidyl trimethylammonium chloride (GTAC) and with phosphoryl chloride ($POCl_3$).

10. The composition of claim 1, wherein the polynucleotide comprises RNA.

11. The composition of claim 1, further comprising one or more selected from water, a biocide, an antimicrobial, an antifungal, a non-polynucleotide pesticide, a chelator, a buffer, a filler, a binder, a hardener, a sticking agent, a pH modifier, a dispersant, a non-ionic surfactant, a zwitterionic surfactant, a defoamer, a silicate, and a photo-protectant.

12. A method of controlling a pest infestation, comprising providing an insecticidally effective amount of the composition of claim 1 in the diet of the pest, wherein the polynucleotide comprises at least 21 contiguous nucleotides that are complementary or identical to a target gene in the pest.

13. The method of claim 12, wherein the pest is a Colorado potato beetle (*Leptinotarsa decemlineata*), a potato leafhopper (*Empoasca fabae*), a potato aphid (*Macrosiphum euphorbiae*), or a green peach aphid (*Myzus persicae*).

14. The method of claim 12, wherein the pest is a flea beetle.

15. The method of claim 12, wherein the composition is applied to a plant surface.

16. The method of claim 12, wherein the composition is applied as a foliar spray or to a seed.

* * * * *